US 7,125,554 B2

(12) United States Patent
Forsberg et al.

(10) Patent No.: US 7,125,554 B2
(45) Date of Patent: Oct. 24, 2006

(54) ENGINEERED SUPERANTIGEN FOR HUMAN THERAPY

(75) Inventors: Goran Forsberg, Eslov (SE); Eva Erlandsson, Dalby (SE); Per Antonsson, Lund (SE); Bjorn Walse, Lund (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 09/900,766

(22) Filed: Jul. 6, 2001

(65) Prior Publication Data

US 2003/0039655 A1 Feb. 27, 2003

(30) Foreign Application Priority Data

Jun. 28, 2001 (SE) .................................. 0102327

(51) Int. Cl.
- A61K 39/395 (2006.01)
- A61K 39/40 (2006.01)
- A61K 39/42 (2006.01)
- C07K 16/00 (2006.01)

(52) U.S. Cl. .............................. 424/183.1; 424/181.1; 530/391.7

(58) Field of Classification Search ............. 530/391.1, 530/391.7, 350; 424/130.1, 133.1, 134.1, 424/135.1, 155.1, 178.1, 180.1, 183.1, 182.1, 424/138.1
See application file for complete search history.

(56) References Cited

U.S. PATENT DOCUMENTS

| | | | |
|---|---|---|---|
| 5,519,114 A | 5/1996 | Johnson et al. |
| 5,545,716 A | 8/1996 | Johnson et al. |
| 5,728,388 A | 3/1998 | Terman |
| 5,858,363 A | 1/1999 | Dohlsten et al. |
| 5,859,207 A | 1/1999 | Johnson et al. |
| 6,042,837 A | 3/2000 | Kalland et al. |
| 6,126,945 A | 10/2000 | Terman et al. |
| 6,180,097 B1 | 1/2001 | Terman |
| 6,197,299 B1 | 3/2001 | Dohlsten et al. |
| 6,221,351 B1 | 4/2001 | Terman |
| 6,251,385 B1 | 6/2001 | Terman |
| 6,338,845 B1 | 1/2002 | Terman |
| 6,340,461 B1 | 1/2002 | Terman |
| 6,399,332 B1 | 6/2002 | Ulrich et al. |
| 6,447,777 B1 | 9/2002 | Terman et al. |
| 6,514,498 B1 * | 2/2003 | Antonsson et al. |
| 6,632,441 B1 | 10/2003 | Schlievert et al. |
| 6,632,640 B1 | 10/2003 | Lee et al. |
| 6,692,746 B1 | 2/2004 | Terman et al. |
| 6,713,284 B1 | 3/2004 | Ulrich et al. |
| 2001/0046501 A1 | 11/2001 | Johnson et al. |
| 2002/0018781 A1 | 2/2002 | Schlievert et al. |
| 2002/0028211 A1 | 3/2002 | Kaempfer et al. |
| 2002/0039585 A1 | 4/2002 | Schlievert et al. |
| 2002/0051765 A1 | 5/2002 | Terman |
| 2002/0058032 A1 | 5/2002 | Hirai et al. |
| 2002/0086813 A1 | 7/2002 | Schlievert et al. |
| 2002/0115190 A1 | 8/2002 | Chen |
| 2002/0141981 A1 | 10/2002 | Lawman et al. |
| 2002/0177551 A1 | 11/2002 | Terman |
| 2003/0009015 A1 | 1/2003 | Ulrich et al. |
| 2003/0036644 A1 | 2/2003 | Ulrich et al. |
| 2003/0039655 A1 | 2/2003 | Forsberg et al. |
| 2003/0092894 A1 | 5/2003 | Antonsson et al. |
| 2003/0124142 A1 | 7/2003 | Fraser et al. |
| 2003/0157113 A1 | 8/2003 | Terman |
| 2004/0142464 A1 | 7/2004 | Lawman et al. |

FOREIGN PATENT DOCUMENTS

| | | |
|---|---|---|
| WO | WO-96/01650 A1 | 1/1996 |
| WO | WO-96/36366 A1 | 11/1996 |
| WO | 97/36932 * | 10/1997 |
| WO | WO-97/36932 A1 | 10/1997 |
| WO | WO-9736032 | 10/1997 |
| WO | WO-99/04820 A2 | 2/1999 |
| WO | WO-01/30854 A2 | 5/2001 |
| WO | WO-01/36486 A2 | 5/2001 |

OTHER PUBLICATIONS

Weinrauch, Y. Annual Review of Microbiology 53:155-87, 1999.*

Sundström, M. et al. The co-crystal of staphylococcal enterotoxin type A with $Zn^2$ at 2.7 ÅResolution; The Journal of Biological Chemistry; vol. 271 No. 50, 1996 pp. 32212-32216.

Sundström, Michael et al. The crystal structure of staphylococcal enterotoxin type D reveals $Zn^{2+}$-mediated homodimerization; The EMBO Journal vol. 15, No. 24, pp. 6832-6840, 1996.

Schad, E.M. et al., Crystal structure of the superantigen staphylococcal enterotoxin type A; The EMBO Journal vol. 14, No. 14, pp. 3292-3301, 1995.

Papageorgiou, A. Microbial superantigens: from structure to function; Trends in Microbiology, vol. 8, No. 8, pp. 369-375, 2000.

Håkansson, M. et al., The Crystal Structure of Staphylococcal Enterotoxin H: Implications for Binding Properties to MHC Class II and TcR Molecules; J. Mol. Biol. 2000; 302, 527-537.

(Continued)

Primary Examiner—Patricia A. Duffy
(74) Attorney, Agent, or Firm—Fulbright & Jaworski LLP

(57) ABSTRACT

The present invention relates to compositions and methods of use, wherein the composition comprises a conjugate of a bacterial superantigen and an antibody moiety. More particularly, the bacterial superantigen has been modified to decrease seroreactivity with retained superantigen activity.

49 Claims, 11 Drawing Sheets

OTHER PUBLICATIONS

Dohlsten, M. et al., Monoclonal antibody-superantigen fusion proteins: Tumor-specific agents for T-cell based tumor therapy; Proc. Natl. Acad. Sci. USA 1994; vol. 91, pp. 8945-8949.

Cavallin, A. et al., The spectral and thermodynamic properties of staphylococcal enterotoxin A, E, and variants suggest that structural modifications are important to control their function; J. Biol Chemistry; 2000; vol. 275, No. 3, pp. 1665-1672.

Burks, E. et al., In vitro scanning saturation mutagenesis of an antibody binding pocket; Proc. Natl. Acad. Sci. USA, 1997. vol. 94, pp. 412-417.

Antonsson, P. et al. Functional characterization of the interaction between the superantigen staphylococcal enterotoxin A and the TCR; J. Immunology; 1997; pp. 4245-4251.

Alpaugh, R. K. et al., Superantigen-targeted Therapy: Phase I escalating repeat dose trial of the fusion protein PNU-214565 in patients with advanced gastrointestinal malignancies; Clinical Cancer Research 1998, Vo. 4 pp. 1903-1914.

Abrahamsen, L. et al., Characterization of two distinct MHC class II binding sites in the superantigen staphylococcal enterotoxin A; The EMBO Journal; 1995, v. 14, No. 13; pp. 2978-2786.

Griggs et al., “Mapping of Multiple Binding Domains of the Superantigen Staphylococcal Enterotoxin a for HLA,” Journal of Immunology vol. 148, 1992, pp. 2516-2521.

Sogaard et al., “Antibody-targeted Superantigens in Cancer Immunotherapy,” Immunotechnology 2, 1996, pp. 151-162.

Hansson et al., “Genetically Engineered Superantigens as Tolerable Antitumor Agents,” Proc. Natl. Acad. Sci. vol. 94, Mar. 1997, pp. 2489-2494.

Rosendahl et al, “Long-Term Survival and Complete Cures of B16 Melanoma-Carrying Animals After Therapy with Tumor-Targeted IL-2 and Sea,” Int. J. Cancer 81, 1999, pp. 156-163.

Forsberg et al., “Therapy of Human Non-small-cell lung Carcinoma Using Antibody Targeting of a Modified Superantigen,” British Journal of Cancer 85 (1), 2001, pp. 129-136.

Third Response to Written Opinion for PCT/SE 02/01188.

Preliminary Examination Report for PCT/SE 02/01188.

U.S. Appl. No. 09/463,470, filed Jan. 21, 2000.

* cited by examiner

```
SEQ ID NO: 2   1-50    SEKSEEINEKDLRKKSELQGTALGNLKQIYYYNSKAITSSEKSADQFLTN
              51-100   TLLFKGFFTGHPWYNDLLVDLGSTAATSEYEGSSVDLYGAYYGYQCAGGT
             101-150   PNKTACMYGGVTLHDNNRLTEEKKVPINLWIDGKQTTVPIDKVKTSKKEV
             151-200   TVQELDLQARHYLHGKFGLYNSDSFGGKVQRGLIVFHSSEGSTVSYDLFD
             201-233   AQGQYPDTLLRIYRDNTTISSTSLSISLYLYTT
```

FIG. 2

```
SEQ ID NO: 3 SEAE18: SEKSEEINEKDLRKKSELQGTALGNLKQIYYYN---EKAITENKESDDQF
SEQ ID NO: 4 SEA   : SEKSEEINEKDLRKKSELQGTALGNLKQIYYYN---EKAKTENKESHDQF
SEQ ID NO: 5 SED   :           ALHKKSELSSTALNNMKHSYADA---NPIIGANKSTGDQF
SEQ ID NO: 6 SEH   :          EDLHDKSELTDLALANAYGQYNHPFIKENIKSDEISGEKDL

SEAE18: LENTLLFKGFFTGHPWYNDLLVDLGSKDATNKYKGKKVDLYGAYYGYQCA
             SEA   : LQHTILFKGFFTDHSWYNDLLVDFDSKDIVDKYKGKKVDLYGAYYGYQCA
             SED   : LENTLLYKAFF--------LLINFNSAEMAQHFKSKNVDVYAIRYAAAC-
             SEH   : IFRNQGDSG--------NDLRVKFATADLAQKFKNKNVDIYGASFYYKCE

SEAE18: GGTPNKTACMYGGVTLHDNNRLTEEKKVPINLWIDGKQTTVPIDKVKTSK
             SEA   : GGTPNKTACMYGGVTLHDNNRLTEEKKVPINLWLDGKQNTVPLETVKTNK
             SED   : -----RTACTYGGVTPHAGNALKARKKIPINLWIIGVQKEVSLDKVQTDK
             SEH   : KISENISECLYGGTTLN-SEKLAQERVIGANVWVDGIQKETE--LIRTNK

SEAE18: KEVTVQELDLQARHYLHGKFGLYNSDSFGGKVQRGLIVFHSSEGSTVSYD
             SEA   : KNVTVQELDLQARRYLQEKYNLYNSDVFDGKVQRGLIVFHTSTEPSVNYD
             SED   : KNVTVQELDAQARRYLQKDLKLYN------AIQRGKLEFDSAAASKVSYD
             SEH   : KNVTLQELDIKIRKILSDKYKIYY---KDSEISKGLIEFDMKTPRDYSFD

SEAE18: LFDAQGQYPDTLLRIYRDNKTINSEN-LHIALYLYTT
             SEA   : LFGAQGQYSNTLLRIYRDNKTINSENM-HIDIYLYTS
             SED   : LFDVAGDFPEKQLRIYSDNKTLSTEH-LHIDIYLYEA
             SEH   : IYDLKGENDYEIDKIYEDNKTLKSDDISHIDVNLYTKKKV
```

FIG. 3

```
                                                   A                  B
SEQ ID NO: 2  SEA/E-120  SEKSEEINEKDLRKKSELQGTALGNLKQIYYYNSKAITSSEKSADQFLTNTLLFKGFFTG 60
SEQ ID NO: 3  SEA/E-18   SEKSEEINEKDLRKKSELQGTALGNLKQIYYYNEKAITENKESDDQFLENTLLFKGFFTG 60
SEQ ID NO: 7  SEE        SEKSEEINEKDLRKKSELQRNALSNLRQIYYYNEKAITENKESDDQFLENTLLFKGFFTG 60
SEQ ID NO: 4  SEA        SEKSEEINEKDLRKKSELQGTALGNLKQIYYYNEKAKTENKESHDQFLQHTILFKGFFTD 60
                         ****************** .**.**:******.** *..::* **** :*:*******.
                                         C
              SEA/E-120  HPWYNDLLVDLGSTAATSEYEGSSVDLYGAYYGYQCAGGTPNKTACMYGGVTLHDNNRLT 120
              SEA/E-18   HPWYNDLLVDLGSKDATNKYKGKKVDLYGAYYGYQCAGGTPNKTACMYGGVTLHDNNRLT 120
              SEE        HPWYNDLLVDLGSKDATNKYKGKKVDLYGAYYGYQCAGGTPNKTACMYGGVTLHDNNRLT 120
              SEA        HSWYNDLLVDFDSKDIVDKYKGKKVDLYGAYYGYQCAGGTPNKTACMYGGVTLHDNNRLT 120
                         *.********:.*.   ..:*:*..************************************

SEA/E-120  EEKKVPINLWIDGKQTTVPIDKVKTSKKEVTVQELDLQARHYLHGKFGLYNSDSFGGKVQ 180
              SEA/E-18   EEKKVPINLWIDGKQTTVPIDKVKTSKKEVTVQELDLQARHYLHGKFGLYNSDSFGGKVQ 180
              SEE        EEKKVPINLWIDGKQTTVPIDKVKTSKKEVTVQELDLQARHYLHGKFGLYNSDSFGGKVQ 180
              SEA        EEKKVPINLWLDGKQNTVPLETVKTNKKNVTVQELDLQARRYLQEKYNLYNSDVFDGKVQ 180
                         **********:****.***::.***.**:***********:**: *:.***** *.****
                             D                                   E
              SEA/E-120  RGLIVFHSSEGSTVSYDLFDAQGQYPDTLLRIYRDNTTISSTSLSISLYLYTT 233
              SEA/E-18   RGLIVFHSSEGSTVSYDLFDAQGQYPDTLLRIYRDNKTINSENLHIALYLYTT 233
              SEE        RGLIVFHSSEGSTVSYDLFDAQGQYPDTLLRIYRDNKTINSENLHIDLYLYTT 233
              SEA        RGLIVFHTSTEPSVNYDLFGAQGQYSNTLLRIYRDNKTINSENMHIDIYLYTS 233
                         *******:*   .:*.****.*****.:*********.**.*  .:  *  :****:
```

5T4 Variable Heavy chain

| SEQ ID NO: 1 | |
|---|---|
| 1-50 | EVQLQ QSGPD LVKPG ASVKI SCKAS GYSFT GYYMH WVKQS PGKGL EWIGR |
| 51-100 | INPNN GVTLY NQKFK DKATL TVDKS STTAY MELRS LTSED SAVYY CARST |

C242 Constant Heavy chain

| 101-150 | MITNY VMDYW GQGTS VTVSS AKTTP PSVYP LAPGS AAQTN SMVTL GCLVK |
| 151-200 | GYFPE PVTVT WNSGS LSSGV HTFPA VLQSD LYTLS SSVTV PSSTW PSETV |

SEA/E-120

| 201-250 | TCNVA HPASS TKVDK KIVPR DSGGP SEKSE EINEK DLRKK SELQG TALGN |
| 251-300 | LKQIY YYNSK AITSS EKSAD QFLTN TLLFK GFFTG HPWYN DLLVD LGSTA |
| 301-350 | ATSEY EGSSV DLYGA YYGYQ CAGGT PNKTA CMYGG VTLHD NNRLT EEKKV |
| 351-400 | PINLW IDGKQ TTVPI DKVKT SKKEV TVQEL DLQAR HYLHG KFGLY NSDSF |
| 401-450 | GGKVQ RGLIV FHSSE GSTVS YDLFD AQGQY PDTLL RIYRD NTTIS STSLS |

5T4 Variable Light chain

| 451-500 | ISLYL YTTSI VMTQT PTSLL VSAGD RVTIT CKASQ SVSND VAWYQ QKPGQ |
| 501-550 | SPKLL ISYTS SRYAG VPDRF SGSGY GTDFT LTISS VQAED AAVYF CQQDY |

C242 Constant Light chain

| 551-600 | NSPPT FGGGT KLEIK RADAA PTVSI FPPSS EQLTS GGASV VCFLN NFYPK |
| 601-650 | DINVK WKIDG SERQN GVLNS WTDQD SKDST YSMSS TLTLT KDEYE RHNSY |
| 651-672 | TCEAT HKTST SPIVK SFNRN ES |

FIG. 10

ENGINEERED SUPERANTIGEN FOR HUMAN THERAPY

BACKGROUND OF THE INVENTION

This application claims priority to the Swedish Application entitled "A Novel Engineered Superantigen for Human Therapy", filing No. 0102327-4 filed Jun. 28, 2001, which is incorporated herein by reference in its entirety.

1. Field of the Invention

The present invention relates to the field of immunology and proliferative diseases, such as cancer. More particularly, it relates to compositions and methods of use, wherein the compositions comprise superantigens that have been modified to reduce seroreactivity.

2. Related Art

Superantigens (SAg's) constitute a group of bacterial and viral proteins that are extremely efficient in activating a large fraction of the T-cell population. Superantigens bind directly to the major histocompatibility complex (MHC) without being processed. In fact, the superantigens bind unprocessed outside the antigen-binding groove on the MHC class II molecules, thereby avoiding most of the polymorphism in the conventional peptide-binding site. The mechanism of binding depends on the superantigen binding to the T-cell receptor (TCR) in the Vβ chain, instead of binding to the hypervariable loops of the T-cell receptor (TCR).

Staphylococcal enterotoxins (SEs) are a homologous group of superantigens, with regard to both structure and function (Papageorgiou et al., 2000). They are known to be the major cause of food poisoning and toxic shock syndrome in humans.

A novel SAg-based tumor therapeutic approach has been developed for the adjuvant treatment of solid tumors. It utilizes both main arms of the immune system by incorporating the Fab part of a tumor-specific monoclonal antibody and a T-cell activating SAg in a single recombinant fusion protein. Fab-SAg proteins bound to tumor cells can trigger SAg-activated cytotoxic T-cells to kill the tumor cells directly by superantigen antibody-dependent cell mediated cytotoxicity, SADCC. In addition, activated T-cells produce tumoricidal and pro-inflammatory cytokines counteracting the problems of tumor heterogeneity, and macromolecular uptake, respectively.

Superantigen-based tumor therapeutics have had some success, however, one clinical problem that needs to be addressed is the activation of the systemic immune system. Fusion proteins with wildtype SEA have been investigated in clinical trials of colorectal and pancreatic cancer (Alpaugh et al., 1998). Even though encouraging results were obtained, limitations have been observed. Firstly, the product was very toxic. Secondly, preformed antibodies against the superantigens in the patients made the dosing complex. In addition, the product was immunogenic. Therefore repeated cycles of therapy was only possible in a limited number of patients.

Until the present invention, SAg-based therapies were dose-limiting. The present invention is the first to modify a superantigen resulting in decreased seroreactivity with retained superantigen activity; thus, the present invention is novel and non-obvious.

BRIEF SUMMARY OF THE INVENTION

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilised as a basis for modifying or designing other structures for carrying out the same purposes of the present invention. It should also be realised by those skilled in the art that such equivalent constructions do not depart from the spirit and scope of the invention as set forth in the appended claims. The novel features which are believed to be characteristic of the invention, both as to its organisation and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

In the present invention, it is provided a conjugate comprising a bacterial superantigen and an antibody moiety, wherein the superantigen is a low titer superantigen comprising regions A to E, which region A is a TCR binding site, and regions B to E determine the binding to MHC class II molecules; and the DNA sequence coding for the superantigen is substituted so that no more than 15 amino acid residues in region A are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. Examples of superantigens include, but are not limited to a staphylococcal enterotoxin (SE), a *Streptococcus pyogenes* exotoxin (SPE), a *Staphylococcus aureus* toxic shock-syndrome toxin (TSST-1), a streptococcal mitogenic exotoxin (SME) and a streptococcal superantigen (SSA). In specific embodiments, the staphylococcal enterotoxin is staphylococcal enterotoxin A (SEA) or staphylococcal enterotoxin E (SEE).

In specific embodiments, the amino acid residue positions in region A to be replaced are selected from the group consisting of 20, 21, 24, 27, 173 and 204. It is also contemplated that region C may comprise substitutions in no more than 15 amino acid residues. These substitutions may occur at the amino acid residue positions of 79, 81, 83 and 84. Yet further, region E may comprise substitutions of no more than 15 amino acid residues, in which a substitution may occur at amino acid residue position 227.

In another embodiment of the present invention, it is provided a conjugate comprising a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region B are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. Specifically, the amino acid residue positions in region B to be replaced may be selected from the group consisting of 34, 35, 39, 40, 41, 42, 44, 45 and 49.

Another embodiment of the present invention, provides a conjugate comprising a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region C are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. In specific embodiments the cancer is selected from the group consisting of lung, breast, colon, kidney, pancreatic, ovarian, stomach, cervix and prostate cancer. The amino acid residue positions in region C to be replaced are selected from the group consisting of 74, 75, 78, 79, 81, 83 and 84.

Examples of superantigens include, but are not limited to staphylococcal enterotoxin (SE), a *Streptococcus pyogenes* exotoxin (SPE), a *Staphylococcus aureus* toxic shock-syndrome toxin (TSST-1), a streptococcal mitogenic exotoxin (SME) and a streptococcal superantigen (SSA). In specific embodiments, the staphylococcal enterotoxin is staphylococcal enterotoxin A (SEA) or staphylococcal enterotoxin E (SEE).

In specific embodiments, the conjugate may further comprise substitutions of no more than 15 amino acid residues in region A. The substitutions in region A may occur at the amino acid residue positions 20, 21, 24, 27, 173 or 204. Yet further, the conjugate may comprise substitutions of no more than 15 amino acid residues in region E. More particularly, the substitution of region E may occur at amino acid residue position 227.

In a further specific embodiment, the conjugate may comprise the SEE amino acid sequence including the substitutions of R20G, N21T, S24G, R27K, K79E, K81E, K83S, K84S and D227S or the SEE amino acid sequence including the substitutions of R20G, N21T, S24G, R27K, K79E, K81E, K83S, K84S and D227A. Yet further, the conjugate may comprise the amino acid sequence of SEQ ID NO: 2.

In further embodiments, the conjugate may comprise an antibody moiety, for example, but not limited to the Fab fragment. Specific Fab fragments may include C215Fab or 5T4Fab. Yet further, the conjugate may comprise the amino acid sequence of SEQ ID NO: 1.

Yet further, the conjugate may also comprise a cytokine, such as interleukin. In specific embodiments, the interleukin is IL2 or a derivative thereof having essentially the same biological activity of native IL2.

Another embodiment comprises a conjugate comprising a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region D are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. The amino acid residue positions in region D to be replaced are selected from the group consisting of 187, 188, 189 and 190.

In another embodiment, it is provided a conjugate comprising a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region E are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. In specific embodiments the staphylococcal enterotoxin is staphylococcal enterotoxin A (SEA) or staphylococcal enterotoxin E (SEE). Also, the amino acid residue positions in region E to be replaced are selected from the group consisting of 217, 220, 222, 223, 225 and 227.

In a specific embodiment, the conjugate further comprises substitutions of no more than 15 amino acid residues in region A. Specifically, the substitutions in region A may occur at the amino acid residue positions of 20, 21, 24, 27, 173 and 204.

In another specific embodiment, the conjugate further comprises substitutions of no more than 15 amino acid residues in region B in which the substitutions may occur at the amino acid residue positions of 34, 35, 39, 40, 41, 42, 44, 45 and 49.

Yet further, the conjugate may comprise substitutions of no more than 15 amino acid residues in region C. Specifically, the substitutions in region C occurs at the amino acid residue positions of 74, 75, 78, 79, 81, 83 and 84. Also, the conjugate may further comprise substitutions of no more than 15 amino acid residues in region D, in which the substitutions may occur at the amino acid residue positions of 187, 188, 189 and 190.

In other specific embodiment, it is provided a pharmaceutical composition comprising a therapeutically effective amount of a conjugate, wherein said conjugate comprises a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region C are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. Specifically, the amino acid residue positions in region C to be replaced are selected from the group consisting of 74, 75, 78, 79, 81, 83 and 84.

In further embodiments, the pharmaceutical composition may comprise a conjugate comprising substitutions of no more than 15 amino acid residues in region A, in which the substitutions in region A occur at the amino acid residue positions of 20, 21, 24, 27, 173 and 204. Yet further, the pharmaceutical composition may also comprise substitutions of no more than 15 amino acid residues in region E. Specifically, the substitution of region E may be at amino acid residue position 227.

In specific embodiments, the pharmaceutical composition may comprise a conjugate comprising the SEE amino acid sequence (SEQ ID NO: 7) as well as the additional substitutions of R20G, N21T, S24G, R27K, K79E, K81E, K83S, K84S and D227S.

In another specific embodiment, the pharmaceutical composition may comprise the SEE amino acid sequence (SEQ ID NO: 7) as well as the additional substitutions of R20G, N21T, S24G, R27K, K79E, K81E, K83S, K84S and D227A. Yet further, the pharmaceutical composition comprises a conjugate that has the amino acid sequence of SEQ ID NO: 2.

In further specific embodiments, the pharmaceutical composition comprises an antibody moiety, for example a Fab fragment. Specifically, the Fab fragment is C215Fab or 5T4Fab. Yet further, the pharmaceutical composition comprises a conjugate that has the amino acid sequence of SEQ ID NO: 1. The pharmaceutical composition may further comprise a cytokine, such as an interleukin. The interleukin may be IL2 or a derivative thereof having essentially the same biological activity of native IL2.

Another embodiment of the present invention includes a method of treating cancer in a mammal by activation of the immune system of said mammal comprising administering to said mammal a therapeutically effective amount of a conjugate, wherein said conjugate comprises a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region C are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure. Examples of cancer include, but are not limited to lung, breast, colon, kidney, pancreatic, ovarian, stomach, cervix and prostate cancer. Specifically, the amino acid residue positions in region C to be replaced are selected from the group consisting of 74, 75, 78, 79, 81, 83 and 84.

In further embodiments, region A may also comprise substitutions of no more than 15 amino acid residues, in which the substitutions occur at the amino acid residue positions of 20, 21, 24, 27, 173 and 204. Also, region E may further comprise substitutions of no more than 15 amino acid residues. Specifically, a substitution of region E may be at amino acid residue position 227. The conjugate may comprise the SEE amino acid sequence (SEQ ID NO: 7) as well as the additional substitutions of R20G, N21T, S24G, R27K, K79E, K81E, K83S, K84S and D227S or the substitutions of R20G, N21T, S24G, R27K, K79E, K81E, K83S, K84S and D227A. Yet further, the conjugate has the amino acid sequence of SEQ ID NO: 2. Yet further, the conjugate may comprise an antibody moiety, for example, but not limited to the Fab fragment. Specific Fab fragments may include C215Fab or 5T4Fab. More particularly, the conjugate may comprise the amino acid sequence of SEQ ID NO: 1.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 is the seven different peptides identified, displayed as lines above the amino acid sequence for SEA/E-120. Characters in light gray indicate which residues have been altered in SEA/E-120 compared to SEA/E-18.

FIG. 3 is a structural sequence alignment of SEA, SED and SEH used as templates to construct the comparative computer model of SEA/E-18. Structural conserved regions are marked with black boxes.

FIG. 4 is a multiple sequence alignment of SEA, SEE, SEA/E-18 and SEA/E-120. Displayed as lines above the alignment are the five different regions A–E within which all the substitutions in SEA/E-120 holds.

FIG. 8A illustrates the cytotoxicity as measured in a superantigen antibody dependent cellular cytotoxicity assay, SADCC. FIG. 8B shows the efficiency of superantigens to mediate T cell killing of MHC class II expressing cells results in systemic cytotoxicity that could cause side effects measured in a Superantigen dependent cellular cytotoxicity assay, SDCC. All new chimeras lowered their effect in the SDCC with at least Hog and with as much as 3log for C215FabSEA/E-120.

FIG. 10 is an amino acid sequence of 5T4FabSEA/E-120 (SEQ ID NO: 1) with the variable parts from the murine 5T4 antibody and the constant parts from the murine C242 antibody. Positions 1–458 is chain A and positions 459–672 is chain B.

DETAILED DESCRIPTION OF THE INVENTION

Figure 1:
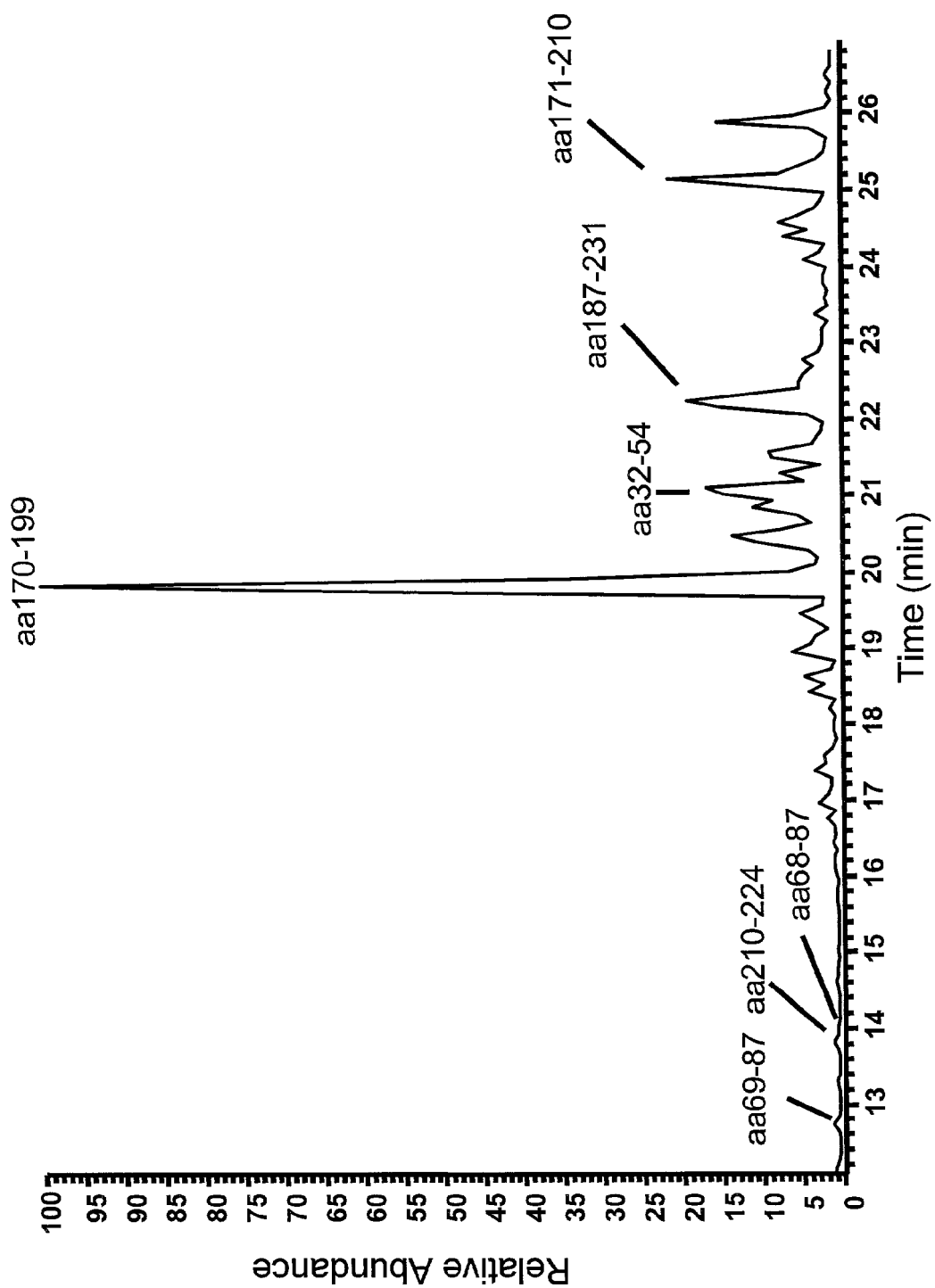
FIG. 1 shows peptide fragments recognized by human anti-SEA that were identified from a pepsin-digest of SEA/E-18 eluted from an anti-SEA column. The fragments were identified both before and after purification using reversed phase HPLC coupled to a mass spectrometer (MS). Fragments found in the digest at the same retention time both before and after affinity purification were considered as positives.

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "antibody" as used herein, refers to an immunoglobulin molecule, which is able to specifically bind to a specific epitope on an antigen. As used herein, an antibody is intended to refer broadly to any immunologic binding agent such as IgG, IgM, IgA, IgD and IgE. Antibodies can be intact immunoglobulins derived from natural sources or from recombinant sources and can be immunoactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Bird et al., 1988).

The term "antigen" as used herein is defined as a molecule that provokes an immune response. This immune response may involve antibody production, the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins, can serve as antigens. Furthermore, antigens can be derived from recombinant DNA The term "cancer" as used herein is defined as a proliferative disease or a malignant neoplasm (tumor). Examples include but are not limited to, breast cancer, prostate cancer, ovarian cancer, cervical cancer, skin cancer, pancreatic cancer, colorectal cancer and lung cancer.

The term "conjugate" as used herein is defined as a fusion protein of a superantigen or a variant of a superantigen fused or conjugated to an antibody or a fragment of an antibody.

The term "immunogenic" or "immunogenicity" as used herein is defined as a substance or a molecule that evokes an immune response.

The term "major histocompatibility complex", or "MHC", as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

The term "seroreactive", "seroreaction" or "seroreactivity" as used herein is defined as a reaction or action occurring as a result of serum or sera. One skilled in the art realizes that the serum or sera of a patient or animal contains neutralizing antibodies or preformed antibodies or endogenous antibodies to a variety of antigens or molecules. Thus, seroreactivity relates to the reaction of neutralizing antibodies in the serum.

The term "superantigen" as used herein is defined as a class of molecules that stimulate a subset of T-cells by binding to MHC class II molecules and Vβ domains of T-cell receptors, stimulating the activation of T-cells expressing particular Vβ V gene segments.

The term "T-cell receptor" as used herein is defined as a receptor that consists of a disulfide-linked heterodimer of the highly variable α or β chains expressed at the cell membrane as a complex with the invariant CD3 chains. T-cells carrying this type of receptor are often called α:β T-cells. An alternative receptor made up of variable γ and δ chains is expressed CD3 on a subset of T-cells.

The term "therapeutically effective" as used herein is defined as the amount of the pharmaceutical composition that is effective at treating a disease or a condition.

The term "variant" or "variants" as used herein refers to proteins or peptides that differ from a reference protein or peptide respectively. Variants in this sense are described below and elsewhere in the present disclosure in greater detail. For example, changes in the nucleic acid sequence of the variant may be silent, i.e., they may not alter the amino acids encoded by the nucleic acid sequence. Where alterations are limited to silent changes of this type a variant will encode a peptide with the same amino acid sequence as the reference peptide. Changes in the nucleic acid sequence of the variant may alter the amino acid sequence of a peptide encoded by the reference nucleic acid sequence. Such nucleic acid changes may result in amino acid substitutions, additions, deletions, fusions and truncations in the peptide encoded by the reference sequence, as discussed below. Generally, differences in amino acid sequences are limited so that the sequences of the reference and the variant are closely similar overall and, in many regions, identical. A variant and reference peptide may differ in amino acid sequence by one or more substitutions, additions, deletions, fusions and truncations, which may be present in any combination. A variant may also be a fragment of a peptide of the invention that differs from a reference peptide sequence by being shorter than the reference sequence, such as by a terminal or internal deletion. Another variant of a peptide of the invention also includes a peptide which retains essentially the same function or activity as such peptide. A variant may also be (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature peptide is fused with another compound, such as a compound to increase the half-life of the peptide (for example, polyethylene glycol), or (iv) one in which the additional amino acids are fused to the mature peptide, such as a leader or secretory sequence or a sequence which is employed for purification of the mature peptide. Variants may be made by mutagenesis techniques, including those applied to nucleic acids, amino acids, cells or organisms, or may be made by recombinant means. All such variants defined above are deemed to be within the scope of those skilled in the art from the teachings herein and from the art.

The term "biological activity" as used herein refers to an intrinsic property of a specific molecule, e.g., activation of certain cells or binding to certain receptors. The definition, as used herein, is primarily qualitative rather than quantitative.

I. Modification of Superantigens

The present invention is drawn to modifying superantigens by lowering their immunogenicity by reducing their seroreactivity. One skilled in the art is cognizant that seroreactivity refers to the reaction of molecules or antigens with neutralizing antibodies in the sera.

Specifically the present invention is drawn to a conjugate comprising a bacterial superantigen and an antibody moiety, wherein the superantigen is a low titer superantigen comprising regions A to E, which region A is a TCR binding site, and regions B to E determine the binding to MHC class II molecules; and the amino acid sequence of the superantigen is substituted so that no more than 15 amino acid residues in region A to E are replaced with different amino acids, such that the substituted superantigen has reduced seroreactivity compared to the superantigen from which it is derived; and wherein the antibody moiety is a full length antibody or any other molecule binding antibody active fragment, which is directed against a cancer-associated cell surface structure.

A. Superantigens

The bacterial superantigens that are contemplated for use in the present invention include, but are not limited to a staphylococcal enterotoxin (SE), a *Streptococcus pyogenes* exotoxin (SPE), a *Staphylococcus aureus* toxic shock-syndrome toxin (TSST-1), a streptococcal mitogenic exotoxin (5MB) and a streptococcal superantigen (SSA). One of skill in the art realizes that the three dimensional structures of the above listed superantigens can be obtained from the Protein Data Bank. Yet further, one skilled in the art can obtain the nucleic acid sequences and the amino acid sequences of the above listed superantigens and other superantigens from GenBank.

In specific embodiments, the superantigen is a low titer superantigen. It is known and understood by those of skill in the art that the sera of humans normally contain high titers of antibodies against superantigens. For the staphylococcal superantigens, for instance, the relative titers are TSST-1>SEB>SEC-1>SEC2>SEA>SED>SEE. One skilled in the art realizes that these relative titers indicate immunogenicity problems and problems with seroreactivity or problems with neutralizing antibodies. Thus, the present invention contemplates using a low titer superantigen, such as SEA or SEE to avoid the seroreactivity of parenterally administered superantigens.

Yet further, it is clearly known and understood that the protein sequences and immunological cross-reactivity of the superantigens or staphylococcal enterotoxins are divided into two related groups. One group consists of SEA, SEE, SED and SEH. The second group is SPEA, SEC, SEB and SSA. Thus, the present invention also contemplates the use of low titer superantigens to decrease or eliminate the cross-reactivity of the present invention with high titer or endogenous antibodies against staphylococcal enterotoxins.

B. Variants of Superantigens

Amino acid sequence variants of the superantigen proteins can be substitutional, insertional or deletion variants. These variants may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

It is thus contemplated by the inventors that various changes may be made in the DNA sequences of genes without appreciable loss of the biological utility or activity of the proteins, as discussed below. The activity being the induction of the T-cell responses to result in cytotoxicity of the tumor cells. Yet further, the affinity of the superantigen for the MHC class II molecules is decreased with minimal effects on the cytotoxicity of the superantigen.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

C. Fusion Proteins

A specialized kind of insertional variant is the fusion protein. This molecule generally has all or a substantial portion of the native molecule, linked at the N- or C-terminus, to all or a portion of a second polypeptide. For example, a fusion protein of the present invention includes the addition of an immunologically active domain, such as an antibody fragment, to target specific tumor cells.

Yet further, inclusion of a cleavage site at or near the fusion junction will facilitate removal of the extraneous polypeptide after purification. Other useful fusions include linking of functional domains, such as active sites from enzymes, glycosylation domains, other cellular targeting signals or transmembrane regions.

D. Domain Switching

An interesting series of variants can be created by substituting homologous regions of various proteins. This is known, in certain contexts, as "domain switching."

Domain switching involves the generation of chimeric molecules using different but, in this case, related polypeptides. By comparing various SAg proteins, one can make predictions as to the functionally significant regions of these molecules. It is possible, then, to switch related domains of these molecules in an effort to determine the criticality of these regions to SAg function. These molecules may have additional value in that these "chimeras" can be distinguished from natural molecules, while possibly providing the same function.

E. Purification of Proteins

It will be desirable to purify the SAg or variants thereof. Protein purification techniques are well known to those of skill in the art. These techniques involve, at one level, the crude fractionation of the cellular milieu to peptide and non-peptide fractions. Having separated the protein from other proteins, the protein of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterised by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesised by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

F. Mutagenesis of Variants

The present invention contemplates that modification of the affinity of the superantigen for the MHC class II molecules may decrease the toxicity of the superantigen. Thus, the decreased affinity for the MHC class II molecules results in decreased seroreactivity or decreased reaction with neutralizing antibodies or endogenous or preformed antibodies.

In specific embodiments mutagenesis will be employed to modify the region of the superantigen that determines binding to the MHC class II molecules. Mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations, which involve the removal, addition or substitution of a single nucleotide base within a DNA sequence, or they may be the consequence of changes involving the insertion or deletion of large numbers of nucleotides.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridisation conditions. The hybridized product is subjected to DNA polymerising enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

In addition to the biological functional equivalents that are produced using mutagenesis techniques discussed above, the present inventors also contemplate that structurally similar compounds may be formulated to mimic the key portions of the superantigen or conjugate of the present invention. Such compounds, which may be termed peptidomimetics, may be used in the same manner as the conjugates of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins. Vita et al. (1998). A structural motif that appears to be evolutionarily conserved in certain toxins is small (30–40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

G. Expression of the Superantigens

The present invention also involves the use of expression vectors and host cells. These expression vectors, which have been genetically engineered to contain the nucleic acid sequence of the conjugates, are introduced or transformed into host cells to produce the conjugates of the present invention.

Host cells can be genetically engineered to incorporate nucleic acid sequences and express peptides of the present invention. Introduction of nucleic acid sequences into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989).

Representative examples of appropriate host cells include bacterial cells, such as streptococci, staphylococci, *E. coli*, streptomyces and *Bacillus subtilis* cells; fungal cells, such as yeast cells and *aspergillus* cells; insect cells such as *Drosophila S2* and Spodoptera Sf9 cells; animal cells such as CHO, COS, HeLa, C127, 3T3, BHK, 293 and Bowes melanoma cells.

II. Cancer Treatment

In the present invention, a superantigen is conjugated to an antibody or a fragment of an antibody to target and destroy cancer cells. Examples of cancer include, but are not limited to lung, breast, colon, kidney, pancreatic, ovarian, stomach, cervix and prostate cancer.

In one aspect of the present invention, the tumor cell must bear some marker that is amenable to targeting, i.e., is not present on the majority of other cells. Many tumor markers exist and any of these may be suitable for targeting in the context of the present invention. Specific targets of the present invention include antibodies. The antibodies that are contemplated in the present invention include, but are not limited to the Fab fragment. Examples of the Fab fragment include C215Fab or 5T4Fab. In addition to Fab, other common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Another aspect of the present invention is to use an immune stimulating molecule as an agent, or more preferably in conjunction with another agent, such as for example, a cytokines such as for example IL-2, IL-4, IL-12, GM-CSF, tumor necrosis factor; interferons alpha, beta, and gamma; F42K and other cytokine analogs; a chemokine such as for example MIP-1, MIP-1beta, MCP-1, RANTES, IL-8; or a growth factor such as for example FLT3 ligand. The stimulating molecule may be conjugated to the conjugate of the present invention or administered as an adjuvant in combination with the conjugate of the present invention.

One particular cytokine contemplated for use in the present invention is IL2 or a derivative have essentially the same biological activity of the native IL2. Interleukin-2 (IL-2), originally designated T-cell growth factor I, is a highly proficient inducer of T-cell proliferation and is a growth factor for all subpopulations of T-lymphocytes. IL-2 is an antigen independent proliferation factor that induces cell cycle progression in resting cells and thus allows clonal expansion of activated T-lymphocytes. Since freshly isolated leukemic cells also secrete IL2 and respond to it IL2 may function as an autocrine growth modulator for these cells capable of worsening ATL. IL2 also promotes the proliferation of activated B-cells although this requires the presence of additional factors, for example, IL4. In vitro IL2 also stimulates the growth of oligodendroglial cells. Due to its effects on T-cells and B-cells IL2 is a central regulator of immune responses. It also plays a role in anti-inflammatory reactions, in hematopoiesis and in tumor surveillance. IL-2 stimulates the synthesis of IFN-$\gamma$ in peripheral leukocytes and also induces the secretion of IL-1, TNF-$\alpha$ and TNF-$\beta$. The induction of the secretion of tumoricidal cytokines, apart from the activity in the expansion of LAK cells, (lymphokine-activated killer cells) are probably the main factors responsible for the antitumor activity of IL2.

It is contemplated that the present invention may be administered to a patient that is suffering from cancer or a proliferative disease. The amount administered to the patient is a therapeutically effective amount or an amount that results in treatment of the cancer or disease. Administration of the conjugate may be via a parenteral or alimentary route. Exemplary alimentary routes include, but are not limited to oral, rectal, sublingual and buccal. Exemplary parenteral routes include, but are not limited to intraperitoneal, intravenous, subcutaneous, intramuscular, intradermal, intratumoral, and intravascular.

III. Pharmaceutical Compositions

The compounds of the present invention may be employed alone or in conjunction with other compounds, such as therapeutic compounds.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils.

Under ordinary conditions of storage and/or use, these preparations contain a preservative to prevent the growth of microorganisms.

The conjugate of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035–1038 and/or 1570–1580). Some variation in dosage will necessarily occur depending on the condition of the subject being treated. The person responsible for administration will, in any event, determine the appropriate dose for the individual subject.

The active conjugate and/or agents may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

In addition to the compounds formulated for parenteral administration, such as intravenous, intraarticular and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilisers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavouring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

In certain embodiments, the use of lipid formulations and/or nanocapsules is contemplated for the introduction of a conjugate/or agents, and/or gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and/or such particles may be easily made.

In an embodiment of the invention, the conjugate may be associated with a lipid. The conjugates associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/conjugate associated compositions of the present invention are not limited to any particular structure in solution. For example, they may be present in a bilayer structure, as micelles, or with a collapsed structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

In the alternative, liposomes can be prepared in accordance with other known laboratory procedures: the method of Bangham et al., (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In vitro Mutagenesis

The different superantigen variants were made using a Polymerase Chain Reaction (PCR) based method.

Briefly, the PCR products contained two unique restriction enzyme sites, one in each end. For the sub-cloning procedure, pUC19 (GIBCO BRL Life Technologies, Middlesex, U.K.) was used, prepared according to QIAprep Spin Miniprep Kit Protocol (QIAGEN, Hilden, Germany). Point mutations not affecting the amino acid sequence were included to facilitate further analyses. The PCR reaction was performed on Perkin Elmer Gene Amp PCR system 2400 with Taq DNA Polymerase and appropriate PCR buffer containing 15 mM $MgCl_2$ (Roche Molecular Biochemicals, Basel, Switzerland). The PCR products and vectors were cleaved overnight with appropriate restriction enzymes. They were purified using electrophoresis in a 1% agarose gel (GIBCO BRL Life Technologies) containing 0.5 µg/ml Ethidiumbromide (Sigma-Aldrich, Steinheim, Germany) in TAE buffer (Sigma-Aldrich). The DNA containing fragment was excised from the gel and extracted using the CONSERT™ Rapid Gel Extraction System (GIBCO BRL Life Technologies). Vector and insert were ligated (T4 DNA ligase, Roche Molecular Biochemicals) at room temperature for 3–4 hours. The ligation mixture was transformed into the *Escherchia coli* strain DH5α (GIBCO BRL Life Technologies) according to instructions enclosed with the cells. Positive clones were verified using DNA sequencing. Correct sequences were cleaved out with RsrII/HindIII at 37° C. overnight and ligated in the expression vector (Dohlsten et al., 1994). The variable parts of the Fab were changed for C215 to suit the in-house animal models. The construct was finally electroporated into the *Escherchia coli* K12 strain UL635 (xyl-7, ara-14, T4R, ΔompT).

Example 2

Identification of Human Anti-SEA Binding Regions

Regions recognized by human anti-SEA were identified from a pepsin-digest of SEA or a chimeric variant of SEA and SEE, SEA/E-18, previously described as SEE/A-A (Antonsson et al., 1997) with the substitution D227A.

Each superantigen was incubated with 0.5% pepsin 10 mM HCl, 150 mM NaCl (w/w) for 60 minutes at 37° C. The peptide mixture was neutralized with 2M Tris-HCl pH 8.0 and applied on a 1 ml HiTrap column (Amersham Pharmacia Biotech, Uppsala, Sweden) with immobilized human anti-SEA. PBS, 8.1 mM $Na_2HPO_4$, 1.5 mM $KH_2PO_4$, 137 mM NaCl, 2.7 mM KCl, pH 7.3 was used as washing buffer and the antibody binding fragments were eluted using 0.1M acetic acid pH 3.0. The fragments were identified both before and after purification using HPLC coupled to a mass spectrometer (MS) (FIG. 1). The chromatography was carried out on a C18 column (2×250 mm) (VYDAC™, Hesperia, Calif., USA) using a linear gradient from 10 to 60% acetonitrile in 0.1% triflouroacetic acid over 30 ml at 40° C. Mass determination was carried out using electrospray MS (Finnigan LCQ, Thermoquest, San Jose, Calif., USA). Fragments found in the digest at the same retention time both before and after affinity purification were considered as positives (FIG. 2).

Example 3

Molecular Modeling

The chimeric superantigen SEA/E-18 was based upon the SEE sequence except for four amino acid residues close to the N-terminus that were from SEA and one substitution in the C-terminal part D227A (FIG. 3 and FIG. 4) (Antonsson et al., 1997).

Figure 5:
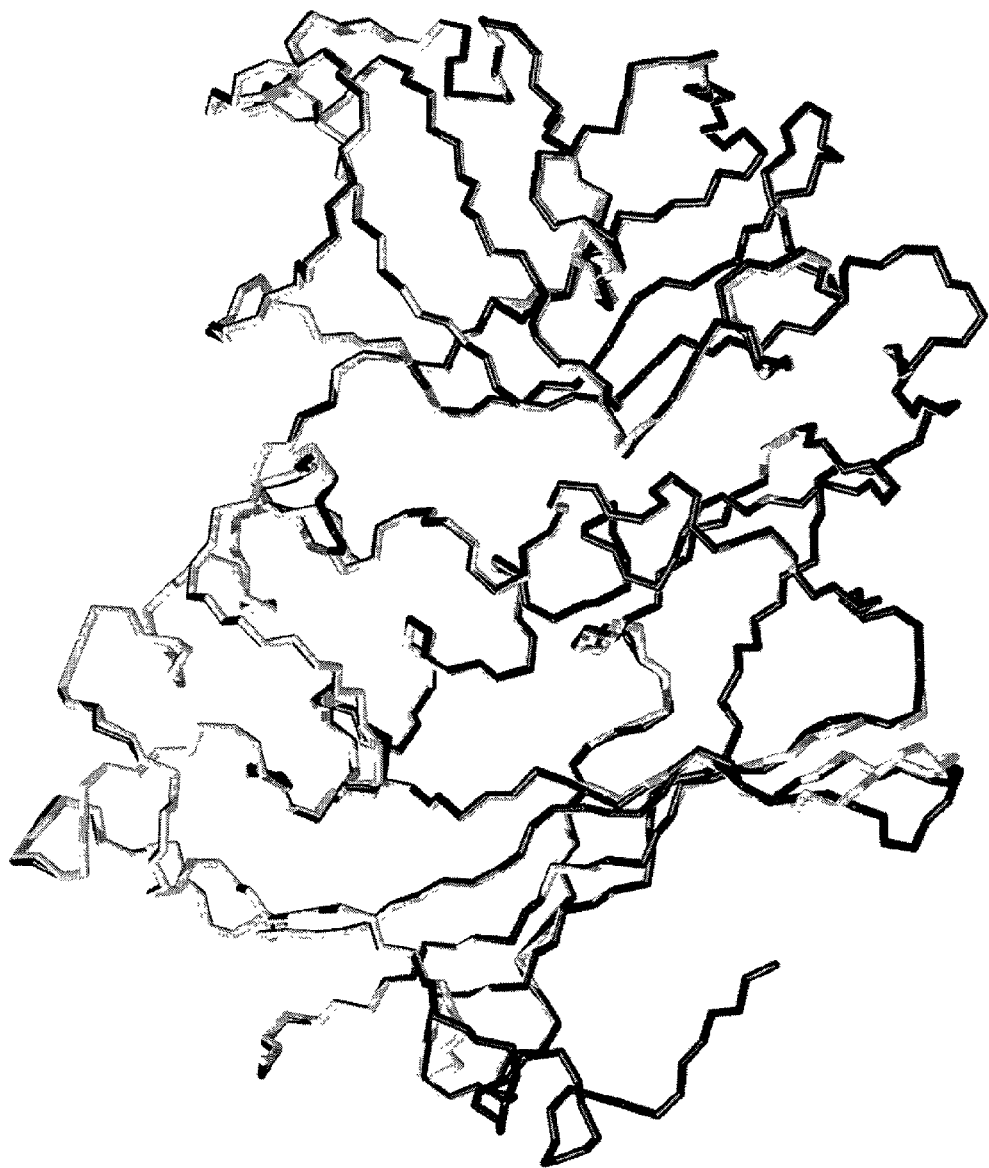
FIG. 5 is a SEA/E-18 model (in black) superimposed on to SEA (1SXT, in gray).

The model construction was performed using the HOMOLOGY module in the INSIGHTII software (MSI, San Diego). Structures for the three superantigens SEA, SED and SEH were aligned and structural conserved regions (SCRs) were determined (FIG. 3). These regions typically mapped to regular secondary structures in the molecules. The raw sequence for SEA/E-18 were loaded and threaded over the SCRs from the SEA structure (FIG. 5). The 1SXT co-ordinates for SEA was used except for the first nine residues in the N-terminus where 1ESF was used. The regions between the SCRs were in most cases flexible loop areas and were built from SEA and SED. Most of the loops were built from SEA except for residues Gln19, Ile140, Asp141, Lys142, Ser189, Gly191, Asp200, Pro206, Asp207 and Leu224, which were built from SED. Some areas within the SCRs showed greater sequence similarity with SED and were therefore built using SED as structural template (Ile37, Glu49, Asn50, Thr51, Leu52, Ser195 and Thr218) (FIG. 3).

Briefly, three-dimensional structures of superantigens with much higher sequence identity to SEE that were available from the PBD were used as templates to construct a homology model of SEAE-18, i.e., SEA (1ESF, Shard et al, 1SXT, Sundstrom et al 1996 A), SED (Sundstrom et al., 1996 B) and SEH (1ENF) (Hakansson et al., 2000). SEA was most similar to SEE with a sequence identity of 80%. SED had a sequence identity of 60% and SEH 50% to SEE.

The final model was tested for bad regions using the PROSTAT module in INSIGHTII. No bad regions were detected. The interior of the protein packed well with no significant difference compared to SEA. All residues end up in allowed regions in a ramachandran plot. Superposition of 1SXT with the model yielded a RMSD of 0.4 Å when Cα atoms were compared. The main difference between the two structures is seen in the β9–β10 loop (residues His187-Thr193) (FIG. 5).

Due to the fact that SEA was used as structural template for most of the residues in SEA/E-18 no problems with overlapping side chains occurred. Splice points before and after the SCRs were repaired. First the substituted side chains were relaxed and then energy minimisation and molecular dynamics simulations relaxed all side chains within the SCRs using standard protocols in HOMOLOGY. Loop areas were relaxed one at a time using first 1000 steps of energy minimization followed by 1000 steps of molecular dynamics. This refinement protocol was applied first on the loop side chains and then on all atoms in the loop. For all simulations the CVFF force field with a force constant of 100 kca/Å2 were used using a time step of 2 fs.

New models of new superantigens variants were constructed using the SEA/E-18 model as a template. The specific amino acid residues were changed directly on the model. The most favorable side chain conformation was selected using a simple steric-hindrance search followed by a short energy minimization.

Example 4

Culturing and Purification

The C215FabSEA/E chimeras were expressed as fusion proteins in the *E. coli* K12 strain UL635 using a plasmid with an IPTG induced Lac UV-5 promoter and a kanamycin resistance gene.

Briefly, bacteria from frozen (–70°) stock solution in 20% glycerol were incubated at 25° C. for 22–24 h in shaker flasks containing (per liter) 2.5 g of $(NH_4)_2SO_4$, 3 g of $KH_2PO_4$, 2 g of $K_2HPO_4$, 0.5 g of sodium citrate, 1 g of $MgSO_4.H_2O$, 0.05 g of kanamycin, 12 g of glucose monohydrate and 1 ml of trace element solution however without $Na_2MoO_4.2H_2O$. The cells were grown to an $Abs_{620}$ of 2–3 and 10 ml of the cultivation medium was used to inoculate a 1 liter fermenter (Belach Bioteknik, Sweden) with a starting volume of 800 ml. The fermenter medium contained (per liter) 2.5 g of $(NH_4)_2SO_4$, 9 g of $K_2HPO_4$, 6 g of $K_2HPO_4$, 0.5 g of sodium citrate, 1 g of $MgSO_4.7H_2O$, 0.05 g of kanamycin, 23.1 g of glucose monohydrate and 1 ml of trace element solution as above. The pH was kept constant at 7.0 by titration of 25% $NH_3$, the aeration was 1 liter/minute and the temperature 25° C. During batch phase the dissolved $O_2$ was kept at 30% by regulating the agitation from 400 rpm to 2000 rpm and during the fed-batch by regulating the feed of glucose (60% w/v). Product formation was induced when the Absorbance at 620 nm was 45 by adding 0.1 mM isopropyl-β-D-thiogalactopyranoside (IPTG). After fermentation the cells were removed by centrifugation at –20° C. prior to purification.

It was applied on a 60 ml protein-G Sepharose 4, fast flow column (Amersham Pharmacia Biotech) with a flow rate of 14 ml/min. The column was washed using PBS and elution was performed with 100 mM acetic acid, 0.025% Tween 20, pH 3.0. The eluted product was collected and the pH was adjusted to 1.5 units below the theoretical isoelectric point with 1M NaOH, filtrated (0.2 μm) and diluted four times with 0.025% Tween 20. Degraded variants were removed using ion-exchange chromatography. The ionic strength of the sample was adjusted to 2 mS/cm and the column used was a SP-Sepharose-HP, Hiload 16/10 (Amersham Pharmacia Biotech). The elution was performed with a flow of 4.0 ml/min for 50 min using a linear gradient from 0–55% buffer B, 100 mM NaAc, 400 mM NaCl, 0.025% Tween 20, pH 5.0 in buffer A, 10 mM NaAc, 0.025% Tween 20, pH 5.0.

The purification procedure was divided into three steps. First DNA was removed from the culture supernatant by 0.19% Polyethyleneimine (w/v) in 0.2M NaCl, pH 7.4, using a peristaltic pump with a flow rate of 12 ml/min. After centrifugation at 7500× g for 30 min, the supernatant was collected.

Example 5

Seroractivity

In a microtiter plate (OptiPlate, Packard Instruments) streptavidin coated PVT beads, 150 μg beads/well (Amersham Pharmacia Biotech) were incubated for 30 min at room temperature with biotin conjugated F(ab)$_2$ fragments of anti-Mouse IgG, 3 μg/mg beads. The beads were preincubated with C215Fab conjugated Superantigens in a 1:2 dilution series, where the highest final concentration in the wells were 40 nM. Finally they were incubated with 1 nM $^{125}$I conjugated affinity purified human anti-SEA antibodies and the amount of β-scintillation was measured in a TopCounter (Packard Instruments).

The reactivity between the superantigen variants and human anti-SEA was measured in a Scintillation Proximity Assay (SPA).

The human anti-SEA reactivity for the Superantigen variants was also measured in an Enzyme-Linked Immunosorbent Assay, ELISA (Cavallin et al., 2000). The results were similar to the ones obtained in the SPA.

Example 6

Biological Function

The ability to induce superantigen antibody dependent cellular cytotoxicity, SADCC and superantigen dependent cellular cytotoxicity, SDCC was compared in a standard 4 h $^{51}$Cr-release assay.

Briefly, the targets that were used for the SDCC were the human B-cell lymphoma Raji cells and the targets for SADCC were human colorectal carcinoma Colo205 cells. The cells were labeled with $^{51}$Cr and diluted to a concentration of 50000 cells/ml to the V-shaped microtiter wells. As effector cells, a SEA reactive human T-cell line, were used at an effector to target ratio of 45:1 for the SADCC and 30:1 for the SDCC. Sag variants were added in concentrations from $10^{-9}$–$10^{-16}$M for the SADCC and from $10^{-7}$–$10^{-14}$M for the SDCC. Supernatants were collected and the release of $^{51}$Cr was measured in a TopCount (Packard Instruments). The percentage of specific cytotoxicity was calculated as 100×[(cpm experimental release–cpm background release)/(cpm total release–cpm background release)].

Example 7

Identification of Antibody Epitopes

In the patients, pre-existing antibodies against superantigens have complicated their clinical application, requiring adjustment of their dosing in therapy (Alpaugh et al, 1998). Another approach to limit the impact of preformed antibodies was to modify the region of the superantigen responsible for T-cell receptor binding (Antonsson et al., 1997). However, the present invention has further improved the therapeutic potential of superantigens by using genetic engineering to remove the antibody epitopes of the superantigen.

It was found that SEE displayed a strong reduction in antibody reactivity compared to SEA (Antonsson et al., 1997). Unfortunately, with this reduction there was also a remarkable decrease in tumor killing properties when fused to a tumor reactive Fab (Antonsson et al, 1997). Therefore chimeric constructs of SEA and SEE were investigated. When introducing the corresponding amino acids from SEA in four positions in the TCR-binding region of SEE, the desired properties were obtained. These substitutions; Arg20Gly, Asn21Thr, Ser24Gly and Arg27Lys (region A) in SEE, resulted in the chimera SEA/E-18 (FIG. 4) (Antonsson et al., 1997). This chimera displayed more than a 50% reduction in antibody reactivity, as in SEE, while retaining the efficient level of cytotoxicity, as in SEA. Additionally, to decrease the affinity between the superantigen and MHC class II, which reduce the SDCC and thereby improve the therapeutic window, SEA/E-18 also contain the substitution Asp227Ala (Abrahmsén et al., 1995).

Figure 6:
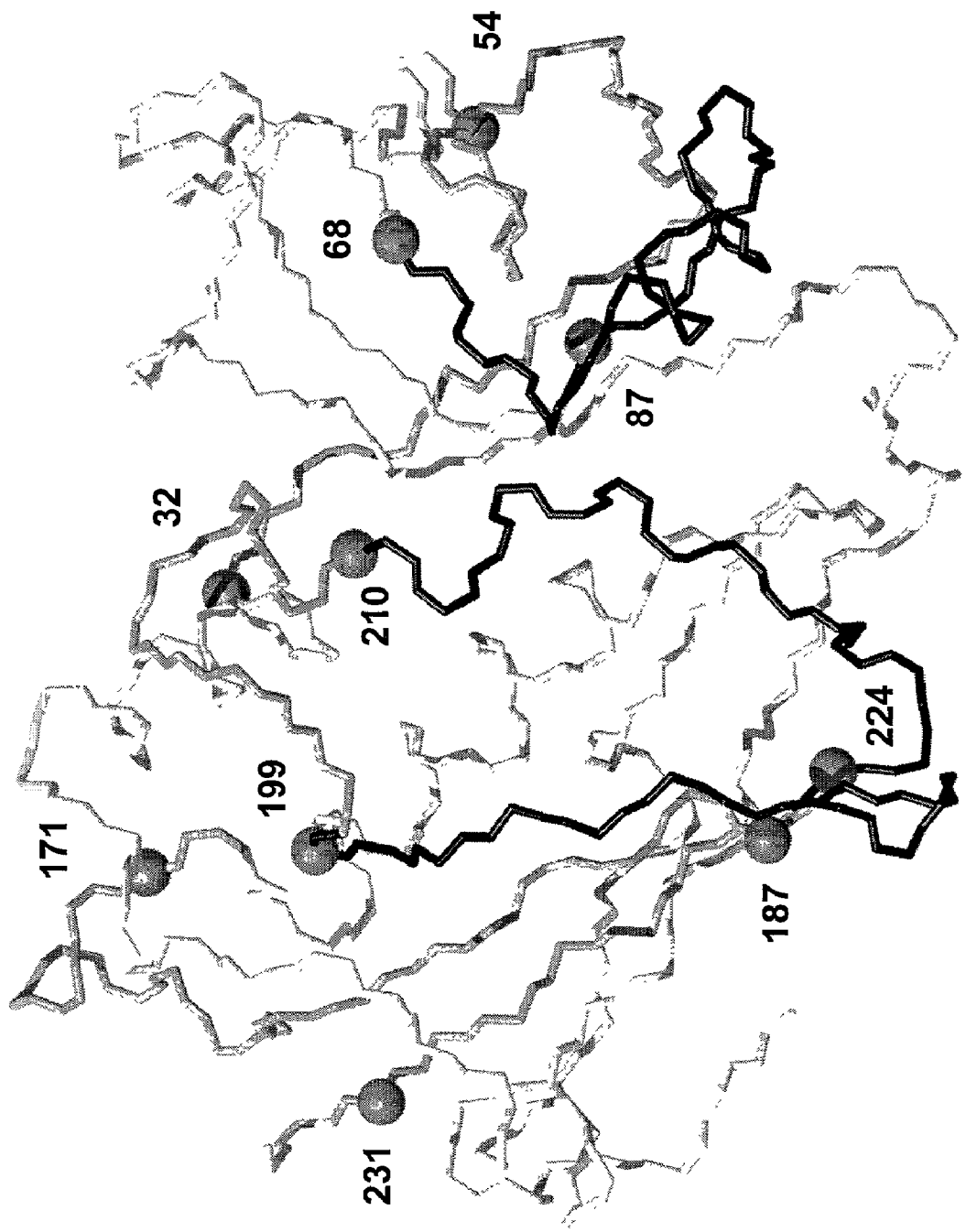
FIG. 6 is the regions of SEA/E-18 that correspond to the identified seroreactivity peptides.

To further decrease the ability of human anti-SEA to recognize SEA/E-18, the antibody binding epitopes within the superantigens were determined. Peptide/fragments from a partial pepsin digest of either SEAwt or SEA/E-18 were captured using immobilized anti-SEA antibodies. After purification, the peptide sequences were identified using LC-MS (FIG. 1). Thereby potential areas involved in antibody recognition were localised in the amino acid sequence. Notably, most of the recovered peptides were located around regions known to be interacting with MHC class II (Abrahmsén et al., 1995) (FIG. 2 and FIG. 6). The three dimensional structure of SEA (Schad et al., 1995; Sundström et al., 1996) and a computer model of SEA/E-18 (FIG. 5), based on the crystal-structure of SEA (Schad et al., 1995; Sundström et al., 1996 A), was used to locate the surface exposed residues within the identified peptides. The following residues were identified as exposed and potential candidates in the antibody binding epitopes: Glu34, Lys35, Glu39, Asn40, Lys41, Glu42, Asp44, Asp45, Glu49, Lys74, Asp75, Asn78, Lys79, Lys81, Lys83, Lys84, Asp173, His187, Ser189, Glu190, Gln204, Lys217, Asn220, Glu222, Asn223, His225 and Asp227 (Table 1).

These residues were subsequently substituted to reduce the binding to antibodies. New computer models with further improved SAg variants were continuously made to confirm and compare the results acquired with the latter. Specifically the influence of side chains was studied and changes effecting the stability of the protein were identified.

Example 8

Modification of the Superantigen to Reduce Seroreactivity

The levels of antibody binding of the identified residues were characterized initially by two to six simultaneous substitutions in SEA/E-18. Thereby the SAg variants SEA/E-62 (Lys217Thr, Asn220Ala, Glu222Thr, Asn223Ala, His225Ala) (region E), SEA/E-63 (Ser189Asp, Glu190Ala) (region D), SEA/E-64 (Glu34Lys, Lys35Glu, Glu39Lys, Asn40Ser, Lys41Glu, Glu42Lys) (region B), SEA/E-65 (Lys79Glu, Lys81Glu, Lys83Glu, Lys84Glu) (region C), SEA/E-74 (Asp44Ala, Asp45Ala, Glu49Thr) (region B) and SEA/E-75 (Lys74Thr, Asp75Ala, Asn78Ser) (region C) were obtained (Table 1, FIG. 4).

Figure 7:
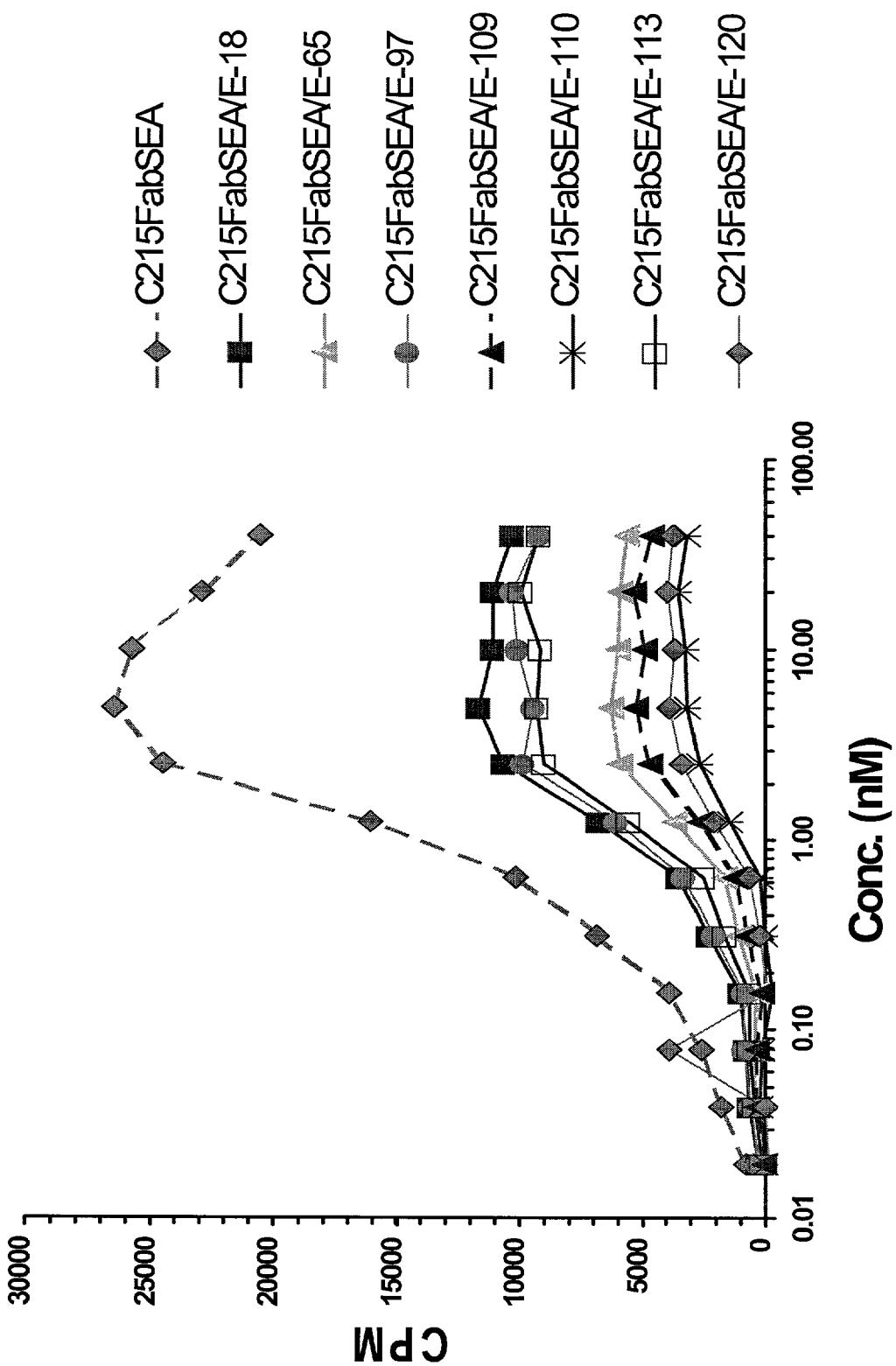
FIG. 7 is a Scintillation Proximity Assay (SPA) that measured the specific binding of $^{125}$I human anti-SEA bound to C215FabSEA, C215FabSEA/E-18, -65, -97, -109, -110, -113 or -120 on biotin conjugated anti-mouseF(ab)$_2$ on streptavidin PVT beads.

To investigate if the anti-SEA antibodies from a human IgG-pool could recognize the different SAg variants, a Scintillation Proximity Assay (SPA) was developed. The modified variants were all recognized to a lower extent compared to SEA/E-18 (Table 1). The most substantial reduction in binding was caused by the substitutions made in SEA/E-65. In the SPA analysis, a reduction with more than 40% was observed (FIG. 7). However, many replacements also generated a reduction in production level of *E. coli* and in addition, the biological activity was occasionally decreased as well. By scrutinising the replacements, the responsible residues within each variant were identified and excluded or modified to achieve better properties. Generally, the production level was increased by hydrophilic replacements compared to more hydrophobic ones.

The reduction in antibody binding was synergistically increased when the variants were combined, as in SEA/E-91 composing of SEA/E-63, SEA/E-65 and a modified SEA/E-74 (with wildtype Asp45) (Table 1). The variant with the most outstanding result in the SPA analysis with a binding reduction of nearly 70% compared to SEA/E-18 was SEA/E-110, a combination of SEA/E-63, SEA/E-75 and modified SEA/E-62 (SEA/E-97), SEA/E-64 (SEA/E-108), SEA/E-65 (SEA/E-84), and SEA/E-74 (wt Asp45) (FIG. 7, Table 1). The modifications responsible for most of the reduction in antibody binding were within SEA/E-109 (Glu34Ser, Glu39Ser, Asn40Ser, Lys41Glu, Glu42Lys, Asp44Ala, Glu49Thr, Lys74Thr, Asp75Ala, Asn78Ser, Lys79Glu, Lys81Glu, Lys83Ser, Lys84Ser) a combination of SEA/E-75 and modified SEA/E-64 (SEA/E-108), SEA/E-65 (SEA/E-84) and SEA/E-74 (wt Asp45). This is because the superantigen variants, containing those substitutions, all displayed a good reduction in the SPA analysis.

Thus, the residues substituted in SEA/E-62, SEA/E-64, SEA/E-65 and SEA/E-74 resulted in between 20 and 40% reduction in antibody reactivity, compared to SEA/E-18 (Table 1).

TABLE 1

| Chimera | E34 | K35 | E39 | N40 | K41 | E42 | D44 | D45 | E49 | K74 | D75 | N78 | K79 | K81 | K83 | K84 | D173 | H187 |
|---|---|---|---|---|---|---|---|---|---|---|---|---|---|---|---|---|---|---|
| SEA/E-21 | | | | | | | | | | | | | | | | | | A |
| SEA/E-62 | | | | | | | | | | | | | | | | | | A |
| SEA/E-97 | | | | | | | | | | | | | | | | | | A |
| SEA/E-63 | | | | | | | | | | | | | | | | | | A |
| SEA/E-64 | K | E | K | S | E | K | | | | | | | | | | | | A |
| SEA/E-108 | S | | S | S | E | K | | | | | | | | | | | | A |
| SEA/E-65 | | | | | | | | | | | | | | E | E | E | E | A |
| SEA/E-90 | | | | | | | | | | | | | | E | E | E | E | A |
| SEA/E-84 | | | | | | | | | | | | | | E | E | S | S | A |
| SEA/E-68 | | | | | | | | | | | | | | | | | A | A |
| SEA/E-74 | | | | | | | | A | A | T | | | | | | | | A |
| SEA/E-91 | | | | | | | | A | | T | | | | E | E | E | E | A |
| SEA/E-75 | | | | | | | | | | T | A | S | | | | | | A |
| SEA/E-93 | | | S | | E | K | A | A | T | | | | | E | E | E | E | A |
| SEA/E-107 | | | | | | | | | | | | | | | | | A | A |
| SEA/E-113 | | | | | | | | | | | | | | | | | A | A |
| SEA/E-109 | S | | S | S | E | K | A | | T | T | A | S | E | E | S | S | | A |
| SEA/E-110 | S | | S | S | E | K | A | | T | T | A | S | E | E | S | S | A | A |
| SEA/E-115 | S | | S | S | E | K | A | | T | T | A | S | E | E | S | S | A | A |
| SEA/E-118 | S | | S | S | E | K | A | | T | T | A | S | E | E | S | S | A | S |
| SEA/E-119 | S | | S | S | E | K | A | | T | T | A | S | E | E | S | S | | A |
| SEA/E-120 | S | | S | S | E | K | A | | T | T | A | S | E | E | S | S | | |
| SEA/E-121 | S | | S | S | E | K | A | | T | T | A | S | E | E | S | S | A | |
| SEA/E-122 | S | | S | S | E | K | A | | T | T | A | S | E | E | S | S | | S |

| Chimera | S188 | S189 | E190 | Q204 | K217 | N220 | E222 | N223 | H225 | D227 | Yield (mg/l) | Seroreactivity (Bmax) | SADCC | SDCC |
|---|---|---|---|---|---|---|---|---|---|---|---|---|---|---|
| SEA/E-21 | T | | | | | | | | | A | 55.0 | 98% | 0.5 | 1 |
| SEA/E-62 | T | | | | T | A | T | A | A | A | 1.0 | 77% | 1 | 0.5 |
| SEA/E-97 | T | | | | T | S | T | S | S | S | 48.0 | 93% | 3 | 1 |
| SEA/E-63 | T | D | A | | | | | | | A | 14.0 | 95% | 1 | 0.5 |
| SEA/E-64 | T | | | | | | | | | A | 23.0 | 68% | 0.5 | 0.5 |
| SEA/E-108 | T | | | | | | | | | A | 30.0 | 66% | 0.7 | 0.9 |
| SEA/E-65 | T | | | | | | | | | A | 1.5 | 57% | 1 | 0.5 |
| SEA/E-90 | T | | | R | | | | | | A | 2.2 | 52% | 1 | 1 |
| SEA/E-84 | T | | | | | | | | | A | 15.0 | 59% | 1 | 1 |
| SEA/E-68 | T | | | | | | | | | A | 26.5 | 93% | 0.5 | 1 |
| SEA/E-74 | T | | | | | | | | | A | 42.0 | 80% | 1 | 0.5 |
| SEA/E-91 | T | D | A | | | | | | | A | 12.0 | 46% | 1 | 0.1 |
| SEA/E-75 | T | | | | | | | | | A | 53.0 | 86% | 0.1 | 1 |
| SEA/E-93 | T | D | A | | | | | | | A | 15.0 | 43% | 1 | none |
| SEA/E-107 | T | D | A | R | T | S | T | S | S | S | 6.0 | 78% | 1 | 0.1 |
| SEA/E-113 | T | D | A | T | T | S | T | S | S | S | 14.0 | 89% | 3 | 0.5 |
| SEA/E-109 | T | | | | | | | | | A | 24.0 | 48% | 1 | 0.04 |
| SEA/E-110 | T | D | A | T | T | S | T | S | S | S | 0.5 | 32% | 0.07 | 0.005 |
| SEA/E-115 | T | | | | T | S | T | S | S | S | 2.0 | 48% | 0.5 | 0.01 |
| SEA/E-118 | T | | | | T | S | T | S | S | S | 2.0 | 46% | 0.5 | 0.005 |
| SEA/E-119 | T | | | | T | S | T | S | S | S | 10.0 | 52% | 1 | 0.05 |
| SEA/E-120 | | | | | T | S | T | S | S | S | 30.0 | 36% | 3 | 0.04 |
| SEA/E-121 | | | | | T | S | T | S | S | S | 7.0 | 44% | 1 | 0.04 |
| SEA/E-122 | | | | | T | S | T | S | S | S | 12.0 | 46% | 1 | 0.006 |

The biological activity has been set to 1 for C215Fab/SEA/E-18 both in the SADC and the SDCC. The value for evaluating the seroreactivity, i.e., Bmax, is expressed in percentages of C215FabSEA/E-18. Values in extra bold type are base on experiments made with a different antibody

Example 9

Replacements Affecting the Production Levels

As indicated above, some of the substitutions on the superantigen surface resulted in decreased levels of production in *E. coli*. Many combinations of such replacements were not even possible to produce. Therefore, it was decided to investigate alternative modifications of those residues apparently causing a reduction in the yield. Substitutions that affected the yield without decreasing the binding to the antibodies were not further investigated. Instead the wild-type residues were used.

In the initial set of superantigen variants, residue Lys35 in SEA/E-64 was affecting the level of expression negatively. When using the wild type residue in position 35 along with serine substitutions of Glu34 and Glu 39, resulting in SAg variant SEA/E-108, there was an increase in yield from 23 mg/l to 30 mg/l. The reduction in antibody reactivity was however maintained. When introducing the glutamic acid substitutions of residues Lys79, Lys81, Lys 83 and Lys 84 in SEA/E-65, this resulted in a production level of only 1.5 mg/l. Due to the fact that the effect in antibody reactivity was decreased with 43% compared to SEA/E-18, effort was made to identify better replacements. The best combination, in respect of both yield and reduced antibody reactivity, was found to be SEA/E-84 with serine residues in position 83 and 84 and preserved glutamic acid in positions 79 and 81 (Table 1). The production level was increased ten times and the antibody reactivity was reduced with 41% compared to SEA/E-18 (Table 1). The production level was increased ten times and the antibody reactivity was reduced with 41% compared to SEA/E-18 (Table 1). The production level was also decreased more than tenfold with the replacements Lys217Thr, Asn220Ala, Glu222Thr, Asn223Ala, His225Ala and Asp227Ala in SEA/E-62, to 1.0 mg/l. However, by replacing the alanine substitutions for serine residues, resulting in SEA/E-97, production yields of 48 mg/ml were obtained (Table 1).

Interestingly, when combining SEA/E-65 with more variants, such as SEA/E-63 and modified SEA/E-74, as in SEA/E-91, the low production level was reversed to 12 mg/l (Table 1). On the other hand, there was only an expression level of superantigen variant SEA/E-110 of 0.5 mg/l and 14 mg/l, respectively. The production level of SEA/E-110 was, however, increased to 30 mg/l when removing the substitutions Asp174Ala, His87Ala, Ser188Thr, Ser189Asp, Glu190Ala and Gln204TAhr creating SEA(E-120 (Table 1).

Introducing a large number of substitutions within the superantigen may lead to problems with *E. coli* expression. There are at least three different mechanisms for this; decreased thermodynamic, destroyed natural folding pathway or newly introduced proteolytic sites. Though the aim with this study was to remove antigenic epitopes on the surface, which most likely would not interfere with any major structural backbones, there was always a possibility that the new structures were depending on other residues than the wild type construct, for maintaining their stability. Therefore, new computer models were constantly made to predict or confirm the location of the substituted residues within the new structure. This way one could identify the responsible residues within the early superantigen variants causing problems with for instance expression levels and accomplish improved variants with either wild type residues or better substitutions (Table 1).

In conclusion, to accomplish a better level of production, the following residues Lys83, Lys84, Asn220, Asn223, His225 and Asp227 should be substituted to serine, not alanine. Additionally, to avoid a reduction in expression levels, the residues Lys35, Asp173, his187, Ser188, Ser189, Glu190 and Gln204 should be conserved.

Example 10

Evaluation of Biological Function Within the Different SAg Variants

Because the superantigens were primarily designed for tumor therapy (Dohlsten et al., 1994), it was important to avoid replacements decreasing tumor directed cytotoxicity within the novel superantigen variants. The ability to mediate this tumor directed cytotoxicity were therefore measured for all new superantigen variants in a SADCC assay (FIG. 3). In addition, the efficiency of superantigens to mediate T cell killing of MHC class II expressing cells results in systemic cytotoxicity that could cause side effects measured in a SDCC assay (FIG. 3). For clinical use, the SDCC should most likely be low to increase the therapeutic window.

Most of the initial set of SAg variants had the same level of tumor specific cytotoxic potency as SEA/E-18 (Table 1). The exceptions were SEA/E-75 with the replacements Lys74Thr, Asp75Ala and Asn78Ser which was decreased tenfold and SEA/E-64, with the replacements Glu34Lys, Lys35Glu, Glu39Lys, Asn40Ser, Lys41Glu and Glu42Lys, which was decreased fivefold compared to SEA/E-18 (Table 1). Interestingly, the decreased activity in SEA/E-75 was only observed in this variant, in combination with further substitutions for example in SEA/E-109 full activity was detected (Table 1). In addition the SDCC activity was unchanged in SEA/E-75 compared to SEA/E-18. The substitutions Lys74Thr, Asp75Ala and Asn78Ser were therefore likely to disturb the interactions important for the antibody dependent cytotoxicity alone.

The majority of the superantigen variants described herein did show a clear reduction in SDCC. A slight decrease in SDCC activity was observed for the initial variants SEA/E-62, SEA/E-63, SEA/E-64, SEA/E-65 and SEA/E-74 in comparison with SEA/E-18.

Figure 8A:
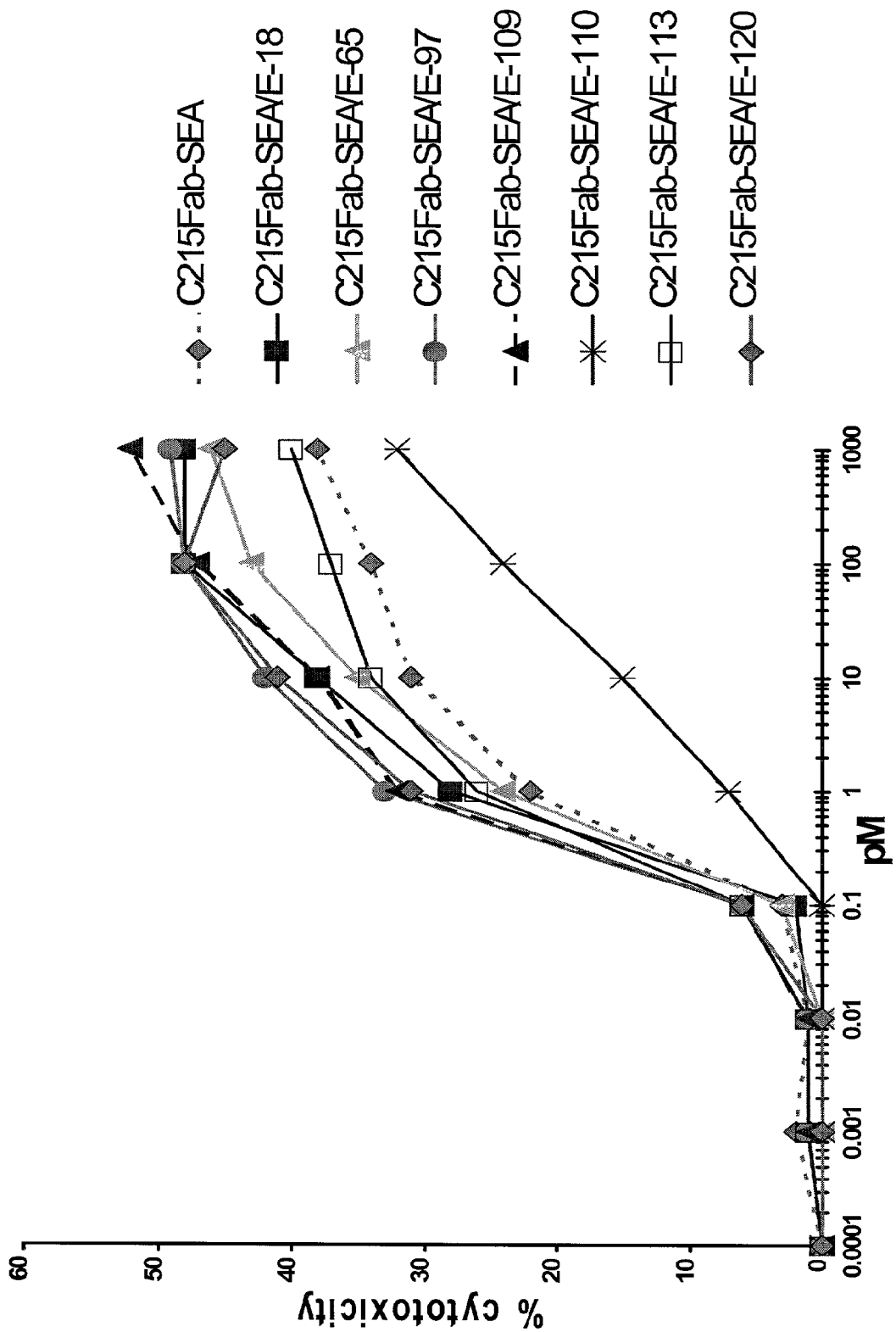
FIG. 8A and FIG. 8B illustrate the ability to mediate tumor directed cytotoxicity.
Figure 8B:
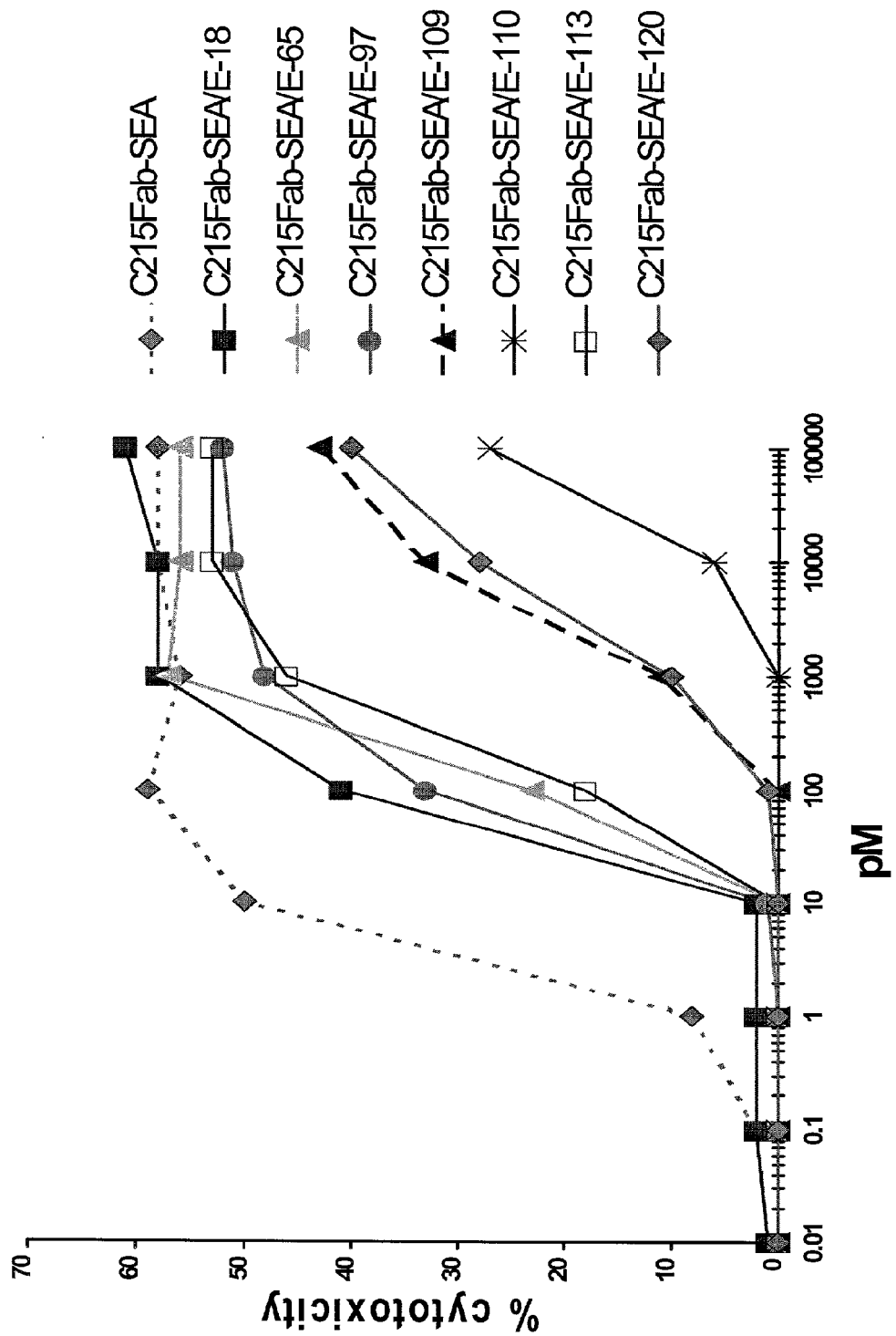

All the superantigen variants contained the substituted residue Asp227Ala or Ser. This substitution was known to reduce the affinity to MHC class II 100 times and thereby the SDCC activity (Abrahmsén et al., 1995). However, since SAg variant SEA/E-109, with the N-terminal substitutions, showed a greater decrease compared to SEA/E-18 than SEA/E-113, with the C-terminal substitutions, this indicated that within SEA/E-109 additional residues have been changed that are important for the SDCC and most likely bind to MHC class II (FIG. 8).

Thus, the residues that caused the greatest reduction were Lys79Ser and Lys81Ser in SEA/E-83 and the substitution Asp45Ala in SEA/E-74. Most of these substitutions are located around the residues that have previously been shown to interact with MHC class II (Abrahmsén et al., 1995).

Example 11

Design of a Novel Superantigen Variant

Figure 9:
FIG. 9 is the ribbon diagram of the SEA/E-120 model. The side chains of residues G20, T21, G24 and K27 are marked in dark gray, side chains of residues S34, S39, S40, E41, K42, A44, T49, T74, A75, S78, E79, E81, S83 and S84 are marked in gray, side chains of residues T217, S220, T222, S223, S225 are marked in black and the side chain of residue S227 are marked in light gray.

In order to design the optimal superantigen variant, all favorable substitutions were combined leading to the superior SEA/E-120 (FIG. 4 and FIG. 9).

First, all favorable modifications in the C-terminal i.e., residues Asp 173Ala, Ser189Thr, Glu190Ala, Lys217Thr, Asn220Ser, Glu222Thr, Asn223Ser, His225Ser and Asp227Ser together with Gln204Thr were assembled forming SAg variant SEA/E-113. This variant exhibited the expected reduction in anti-SEA reactivity and acceptable levels of expression but with a somewhat decreased biological activity (Table 1, FIG. 7 and FIG. 8A and FIG. 8B). All favorable substitutions in the N-terminal i.e., residues Glu34Ser, Glu39Ser, Asn40Ser, Lys41Glu, Glu42Lys, Asp44Ala, Glu49T, Lys74T, Asn78Ser, Lys79Glu, Lys81Glu, Lys83Ser and Lys84Ser were assembled into SEA/E-109. A remarkable decrease in anti-SEA reactivity was observed for this superantigen variant along with a high level of expression and even improved biological profile (Table 1, FIG. 7 and FIG. 8A and FIG. 8B). However, when creating the combination of these two variants SEA/E-113 and SEA/E-109 in SEA/E-110, there was a dramatic loss of both yield and biological function (Table1). The biological potency was fully recovered when wild type residues Ser189, Glu190 and Gln204 were used again in SEA/E-115 (Table1), but production levels were still at a low level. Molecular modeling of this variant suggested that residues Asp173, His187 and Ser188, could be important for the stabilization of the fold and subsequently resulting in higher yields.

Several different combinations were made to evaluate these residues, resulting in SEA/E-118, SEA/E-119, SEA/E-120, SEA/E-121 and SEA/E-122 (Table1). Best production was obtained with SEA/E-120 with wild type residues in all three positions. Together with formerly made SEA/E-21, SEA/E-74, SEA/E-97, SEA/E-108 and SEA/E-109, these were the only SAg variants reaching expression levels of more than 20 mg/l (Table 1). No significant differences in regard of biological activity or antibody reactivity were observed between the variants.

Example 12

Design of a Novel Conjugate

SEA/E-120 was genetically fused to the Fab moiety of the tumor reactive antibody that is 5T4 (Dohlsten et al., 1994) (FIG. 10).

The antigen of 5T4 is expressed on a variety of different tumors, such as non-small cell lung cancer, breast cancer, renal cell cancer, pancreatic cancer, ovarian cancer and colon cancer. Substitutions in the wildtype sequence of 5T4 were also made to accomplish higher yields. In the Heavy chain; His41Pro, Ser44Gly, Ile69Thr and Val113Gly and in the Light chain; Phe10Ser, Thr45Lys, Ile63Ser, Phe73Leu, Thr77Ser, Leu78Val and Leu83Ala.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilised according to the present invention. Accordingly, the appended claims are intended to include within their scope such processes, machines, manufacture, compositions of matter, means, methods, or steps.

REFERENCES CITED

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. Pat. No. 4,554,101
U.S. Pat. No. 5,221,605
U.S. Pat. No. 5,238,808
U.S. Pat. No. 5,798,208
U.S. Pat. No. 5,830,650
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,789,166
U.S. Pat. No. 5,446,128
U.S. Pat. No. 5,710,245
U.S. Pat. No. 5,840,833
U.S. Pat. No. 5,859,184
U.S. Pat. No. 5,440,013
U.S. Pat. No. 5,618,914
U.S. Pat. No. 5,670,155
U.S. Pat. No. 5,475,085
U.S. Pat. No. 5,929,237
U.S. Pat. No. 5,672,681
U.S. Pat. No. 5,674,976
U.S. Pat. No. 4,608,251
U.S. Pat. No. 4,601,903
U.S. Pat. No. 4,599,231
U.S. Pat. No. 4,599,230
U.S. Pat. No. 4,596,792
U.S. Pat. No. 4,578,770
Abrahmsén L., et al. EMBO J. 14:2978–86, 1995.
Alpaugh R. K., et al. Clin Cancer Res. 4:1903–14, 1998.
Antonsson P., et al. *J Immunol* 158:4245–51, 1997.
Bangham et al., *J. Mol. Biol.,* 13:238–252, 1965.
Bird et al., Science. 242:423–6,1988.
Braisted et al, *Proc Natl Acad Sci USA.* 93(12):5688–92, 1996.
Burks et al., *Proc Natl Acad Sci USA.* 94(2):412–7, 1997.
Capaldi et al., *Biochem. Biophys. Res. Comm.,* 76:425, 1977.
Cavallin A., et al. *J Biol Chem.* 275:1665–72, 2000.
Cunningham et al., Science. 244(4908):1081–5, 1989.
Davis et al., Basic Methods in Molecular Biology, 1986
Dohlsten M., et al. *Proc Natl Acad Sci U.S.A.* 91:8945–9, 1994.
DRUG CARRIERS IN BIOLOGY AND MEDICINE, G. Gregoriadis ed. (1979) pp. 287–341.
Hakansson, M. et al. *J Mol Biol.* 302:527–37, 2000.
Harlow, et al. Antibodies: A Laboratory Manual, 1988.
Johannesson et al., *J. Med. Chem.* 42:601–608, 1999.
Kaneda et al., *J Biol Chem.,* 264(21):12126–12129, 1989.
Kato et al., J Biol Chem., 266(6):3361–3364, 1991.
Nicolau et al., *Methods Enzymol.,* 149:157–176, 1987.
Papageorgiou A. C. et al. *Trends in Microbiology* 8: 369–375, 2000.

Remington's Pharmaceutical Sciences, 15th Edition, Chapter 61, pages 1035–1038 and 1570–1580.
Sambrook et. al., In: *Molecular Cloning: A Laboratory Manual*, 2d Ed., 1989.
Schad E. M., et al. *EMBO J* 14:3292–3301, 1995.
Short et al., *J Biol Chem.* 270(48):28541–50, 1995.
Sundstrom M, et al. *EMBO J* 15:6832–40, 1996 A.
Sundstrom M., et al. *J Biol Chem* 271:32212–16, 1996 B.
Szoka and Papahadjopoulos, *Proc. Natl. Acad. Sci.*, 75:4194–4198, 1978.
Vita et al., *Biopolymers* 47:93–100, 1998.
Warren et al., *Biochemistry* 35(27):8855–62, 1996.
Weisshoff et al., *Eur. J. Biochem.* 259:776–788, 1999.
Wells et al., *Methods.* 10(1):126–34, 1996.
Wong et al., *Gene,* 10: 87–94, 1980.
Yelton et al., *J Immunol.* 155(4):1994–2004, 1995.

---

We claim:

1. A conjugate comprising a bacterial superantigen and an antibody, wherein
   the superantigen is a variant of Staphylococcal enterotoxin E, reference SEQ ID NO: 7, and differs from Staphylococcal enterotoxin E in comprising amino acid substitutions as follows, wherein the positions of the amino acid substitutions are relative to the amino acid positions in reference SEQ ID NO: 7:
   (i) amino acid position 20 is glycine or a conserved variant thereof, amino acid position 21 is threonine or a conserved variant thereof, amino acid position 24 is glycine or a conserved variant thereof, amino acid position 27 is lysine or a conserved variant thereof, and amino acid position 227 is serine or alanine, or a conserved variant thereof; and
   (ii) wherein at least one amino acid in a region C is substituted with a different amino acid, such that the superantigen variant has reduced seroreactivity compared to the seroreactivity of Staphylococcal enterotoxin having the amino acid sequence of SEQ ID NO: 7, and the position of the amino acid substitution in region C is selected from the group consisting of amino acid positions 74, 75, 78, 79, 81, 83 and 84;
   and wherein the antibody binds 5T4 cancer antigen.

2. The conjugate of claim 1, wherein the antibody binds 5T4 cancer antigen on a cancer selected from the group consisting of lung, breast, colon, kidney, pancreatic, ovarian, stomach, cervix and prostate cancer.

3. The conjugate of claim 2, wherein the cancer is lung cancer.

4. The conjugate of claim 2, wherein the antibody comprises a full length antibody or an antigen-binding antibody fragment.

5. The conjugate of claim 1, wherein the conjugate comprises SEQ ID NO: 1.

6. The conjugate of claim 1, wherein the substitution at amino acid position 227 is alanine.

7. The conjugate of claim 1, wherein the substitution at amino acid position 227 is serine.

8. The conjugate of claim 1, wherein the superantigen variant further comprises an amino acid substitution in a region E, wherein at least one amino acid in the region E is substituted with a different amino acid, such that the variant has reduced seroreactivity compared to the seroreactivity of Staphylococcal enterotoxin having the amino acid sequence of SEQ ID NO: 7, and the position of the amino acid substitution in region E is selected from the group consisting of amino acid positions 217, 220, 222, 223, and 225.

9. The conjugate of claim 8, wherein the superantigen variant comprises SEQ ID NO: 2.

10. The conjugate of claim 8, wherein the antibody binds 5T4 cancer antigen on a cancer selected from the group consisting of lung, breast, colon, kidney, pancreatic, ovarian, stomach, cervix and prostate cancer.

11. The conjugate of claim 10, wherein the cancer is lung cancer.

12. The conjugate of claim 8, wherein the antibody comprises a full length antibody or an antigen-binding antibody fragment.

13. The conjugate of claim 1, wherein the substituted amino acid in region C comprises an amino acid selected from the group consisting of threonine or a conserved variant thereof at position 74, alanine or a conserved variant thereof at position 75, serine or a conserved variant thereof at position 78, glutamic acid or a conserved variant thereof at position 79, glutamic acid or a conserved variant thereof at position 81, serine or a conserved variant thereof at position 83, serine or a conserved variant thereof at position 84.

14. The conjugate of claim 13, wherein the antibody binds 5T4 cancer antigen on a cancer selected from the group consisting of lung, breast, colon, kidney, pancreatic, ovarian, stomach, cervix and prostate cancer.

15. The conjugate of claim 14, wherein the cancer is lung cancer.

16. The conjugate of claim 14, wherein the antibody comprises a full length antibody or an antigen-binding antibody fragment.

17. The conjugate of claim 8, wherein the substituted amino acid in region E comprises an amino acid selected from the group consisting of threonine or a conserved variant thereof at position 217, serine or a conserved variant thereof at position 220, threonine or a conserved variant thereof at position 222, serine or a conserved variant thereof at position 223, and serine or a conserved variant thereof at position 225.

18. The conjugate of claim 17, wherein the antibody binds 5T4 cancer antigen on a cancer selected from the group consisting of lung, breast, colon, kidney, pancreatic, ovarian, stomach, cervix and prostate cancer.

19. The conjugate of claim 18, wherein the cancer is lung cancer.

20. The conjugate of claim 18, wherein the antibody comprises a full length antibody or an antigen-binding antibody fragment.

21. A composition comprising the conjugate of claim 1 and a carrier.

22. The composition of claim 21, wherein the antibody binds 5T4 cancer antigen on a cancer selected from the group consisting of lung, breast, colon, kidney, pancreatic, ovarian, stomach, cervix and prostate cancer.

23. composition of claim 22, wherein the cancer is lung cancer.

24. The composition of claim 22, wherein the antibody comprises a full length antibody or an antigen-binding antibody fragment.

25. The composition of claim 21, wherein the conjugate comprises SEQ ID NO: 1.

26. The composition of claim 21, wherein the substitution at amino acid position 227 is alanine.

27. The composition of claim 21, wherein the substitution at amino acid position 227 is serine.

28. The composition of claim 21, wherein the superantigen variant further comprises an amino acid substitution in a region E, wherein at least one amino acid in the region B is substituted with a different amino acid, such that the variant has reduced seroreactivity compared to the seroreactivity of Staphylococcal enterotoxin having the amino acid sequence of SEQ ID NO: 7, and the position of the amino acid substitution in region E is selected from the group consisting of amino acid positions 217, 220, 222, 223, 225 and 227.

29. The composition of claim 28, wherein the superantigen variant comprises SEQ ID NO: 2.

30. The composition of claim 28, wherein the antibody binds 5T4 cancer antigen on a cancer selected from the group consisting of lung, breast, colon, kidney, pancreatic, ovarian, stomach, cervix and prostate cancer.

31. The composition of claim 28, wherein the cancer is lung cancer.

32. The composition of claim 28, wherein the antibody comprises a full length antibody or an antigen-binding antibody fragment.

33. The composition of claim 21, wherein the substituted amino acid in region C comprises an amino acid selected from the group consisting of threonine or a conserved variant thereof at position 74, alanine or a conserved variant thereof at position 75, serine or a conserved variant thereof at position 78, glutamic acid or a conserved variant thereof at position 79, glutamic acid or a conserved variant thereof at position 81, serine or a conserved variant thereof at position 83, serine or a conserved variant thereof at position 84.

34. The composition of claim 33, wherein the antibody binds 5T4 cancer antigen on a cancer selected from the group consisting of lung, breast, colon, kidney, pancreatic, ovarian, stomach, cervix and prostate cancer.

35. The composition of claim 34, wherein the cancer is lung cancer.

36. The composition of claim 34, wherein the antibody comprises a full length antibody or an antigen-binding antibody fragment.

37. The composition of claim 28, wherein the substituted amino acid in region E comprises an amino acid selected from the group consisting of threonine or a conserved variant thereof at position 217, serine or a conserved variant thereof at position 220, threonine or a conserved variant thereof at position 222, serine or a conserved variant thereof at position 223, and serine or a conserved variant thereof at position 225.

38. The composition of claim 37, wherein the antibody binds 5T4 cancer antigen on a cancer selected from the group consisting of lung, breast, colon, kidney, pancreatic, ovarian, stomach, cervix and prostate cancer.

39. The composition of claim 38, wherein the cancer is lung cancer.

40. The composition of claim 38, wherein the antibody comprises a full length antibody or an antigen-binding antibody fragment.

41. The composition of claim 22, wherein the carrier is aqueous.

42. The composition of claim 22, wherein the composition is lyophylized.

43. The composition of claim 24, wherein the carrier is aqueous.

44. The composition of claim 25, wherein the carrier is aqueous.

45. The composition of claim 25, wherein the composition is lyophylized.

46. The composition of claim 24, wherein the carrier is aqueous.

47. The composition of claim 26, wherein the carrier is aqueous.

48. The composition of claim 26, wherein the composition is lyophylized.

49. The composition of claim 36, wherein the carrier is aqueous.

* * * * *

UNITED STATES PATENT AND TRADEMARK OFFICE
CERTIFICATE OF CORRECTION

| | | |
|---|---|---|
| PATENT NO. | : 7,125,554 B2 | Page 1 of 1 |
| APPLICATION NO. | : 09/900766 | |
| DATED | : October 24, 2006 | |
| INVENTOR(S) | : Göran Forsberg et al. | |

It is certified that error appears in the above-identified patent and that said Letters Patent is hereby corrected as shown below:

Column 46, line 49, in claim 28, "B" should read -- E --.

Column 46, line 63, in claim 31, "28" should read -- 30 --.

Column 46, line 65, in claim 32, "28" should read -- 30 --.

Column 48, line 19, in claim 46, "24" should read -- 28 --.

Column 48, line 21, in claim 47, "26" should read -- 29 --.

Column 46, line 23, in claim 48, "26" should read -- 29 --.

Signed and Sealed this

Sixth Day of March, 2007

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 672
<212> TYPE: PRT
<213> ORGANISM: Artificial Sequence
<220> FEATURE:
<221> NAME/KEY: PEPTIDE
<222> LOCATION: (1)..(672)
<223> OTHER INFORMATION: Conjugate protein

<400> SEQUENCE: 1

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Ser Gly Gly
    210                 215                 220

Pro Ser Glu Lys Ser Glu Glu Ile Asn Glu Lys Asp Leu Arg Lys Lys
225                 230                 235                 240

Ser Glu Leu Gln Gly Thr Ala Leu Gly Asn Leu Lys Gln Ile Tyr Tyr
                245                 250                 255

Tyr Asn Ser Lys Ala Ile Thr Ser Ser Glu Lys Ser Ala Asp Gln Phe
            260                 265                 270

Leu Thr Asn Thr Leu Leu Phe Lys Gly Phe Phe Thr Gly His Pro Trp
```

```
                275                 280                 285
Tyr Asn Asp Leu Leu Val Asp Leu Gly Ser Thr Ala Ala Thr Ser Glu
    290                 295                 300
Tyr Glu Gly Ser Ser Val Asp Leu Tyr Gly Ala Tyr Tyr Gly Tyr Gln
305                 310                 315                 320
Cys Ala Gly Gly Thr Pro Asn Lys Thr Ala Cys Met Tyr Gly Gly Val
                325                 330                 335
Thr Leu His Asp Asn Asn Arg Leu Thr Glu Glu Lys Lys Val Pro Ile
            340                 345                 350
Asn Leu Trp Ile Asp Gly Lys Gln Thr Val Pro Ile Asp Lys Val
        355                 360                 365
Lys Thr Ser Lys Lys Glu Val Thr Val Gln Glu Leu Asp Leu Gln Ala
    370                 375                 380
Arg His Tyr Leu His Gly Lys Phe Gly Leu Tyr Asn Ser Asp Ser Phe
385                 390                 395                 400
Gly Gly Lys Val Gln Arg Gly Leu Ile Val Phe His Ser Ser Glu Gly
                405                 410                 415
Ser Thr Val Ser Tyr Asp Leu Phe Asp Ala Gln Gly Gln Tyr Pro Asp
            420                 425                 430
Thr Leu Leu Arg Ile Tyr Arg Asp Asn Thr Thr Ile Ser Ser Thr Ser
        435                 440                 445
Leu Ser Ile Ser Leu Tyr Leu Tyr Thr Thr Ser Ile Val Met Thr Gln
    450                 455                 460
Thr Pro Thr Ser Leu Leu Val Ser Ala Gly Asp Arg Val Thr Ile Thr
465                 470                 475                 480
Cys Lys Ala Ser Gln Ser Val Ser Asn Asp Val Ala Trp Tyr Gln Gln
                485                 490                 495
Lys Pro Gly Gln Ser Pro Lys Leu Leu Ile Ser Tyr Thr Ser Ser Arg
            500                 505                 510
Tyr Ala Gly Val Pro Asp Arg Phe Ser Gly Ser Gly Tyr Gly Thr Asp
        515                 520                 525
Phe Thr Leu Thr Ile Ser Ser Val Gln Ala Glu Asp Ala Ala Val Tyr
    530                 535                 540
Phe Cys Gln Gln Asp Tyr Asn Ser Pro Pro Thr Phe Gly Gly Gly Thr
545                 550                 555                 560
Lys Leu Glu Ile Lys Arg Ala Asp Ala Ala Pro Thr Val Ser Ile Phe
                565                 570                 575
Pro Pro Ser Ser Glu Gln Leu Thr Ser Gly Gly Ala Ser Val Val Cys
            580                 585                 590
Phe Leu Asn Asn Phe Tyr Pro Lys Asp Ile Asn Val Lys Trp Lys Ile
        595                 600                 605
Asp Gly Ser Glu Arg Gln Asn Gly Val Leu Asn Ser Trp Thr Asp Gln
    610                 615                 620
Asp Ser Lys Asp Ser Thr Tyr Ser Met Ser Ser Thr Leu Thr Leu Thr
625                 630                 635                 640
Lys Asp Glu Tyr Glu Arg His Asn Ser Tyr Thr Cys Glu Ala Thr His
                645                 650                 655
Lys Thr Ser Thr Ser Pro Ile Val Lys Ser Phe Asn Arg Asn Glu Ser
            660                 665                 670

<210> SEQ ID NO 2
<211> LENGTH: 233
<212> TYPE: PRT
<213> ORGANISM: Artificial Sequence
```

```
<220> FEATURE:
<221> NAME/KEY: Peptide
<222> LOCATION: (1)..(233)
<223> OTHER INFORMATION: Chimeric Protein

<400> SEQUENCE: 2

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Ser Lys Ala Ile Thr Ser Glu Lys Ser Ala Asp Gln Phe Leu
        35                  40                  45

Thr Asn Thr Leu Leu Phe Lys Gly Phe Phe Thr Gly His Pro Trp Tyr
    50                  55                  60

Asn Asp Leu Leu Val Asp Leu Gly Ser Thr Ala Ala Thr Ser Glu Tyr
65                  70                  75                  80

Glu Gly Ser Ser Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Ile Asp Gly Lys Gln Thr Thr Val Pro Ile Asp Lys Val Lys
    130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
            180                 185                 190

Thr Val Ser Tyr Asp Leu Phe Asp Ala Gln Gly Gln Tyr Pro Asp Thr
        195                 200                 205

Leu Leu Arg Ile Tyr Arg Asp Asn Thr Thr Ile Ser Ser Thr Ser Leu
    210                 215                 220

Ser Ile Ser Leu Tyr Leu Tyr Thr Thr
225                 230

<210> SEQ ID NO 3
<211> LENGTH: 233
<212> TYPE: PRT
<213> ORGANISM: Artificial Sequence
<220> FEATURE:
<221> NAME/KEY: peptide
<222> LOCATION: (1)..(233)
<223> OTHER INFORMATION: Chimeric Protein

<400> SEQUENCE: 3

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Ile Thr Glu Asn Lys Glu Ser Asp Asp Gln Phe Leu
        35                  40                  45

Glu Asn Thr Leu Leu Phe Lys Gly Phe Phe Thr Gly His Pro Trp Tyr
    50                  55                  60

Asn Asp Leu Leu Val Asp Leu Gly Ser Lys Asp Ala Thr Asn Lys Tyr
65                  70                  75                  80
```

```
Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Ile Asp Gly Lys Gln Thr Thr Val Pro Ile Asp Lys Val Lys
    130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
            180                 185                 190

Thr Val Ser Tyr Asp Leu Phe Asp Ala Gln Gly Gln Tyr Pro Asp Thr
        195                 200                 205

Leu Leu Arg Ile Tyr Arg Asp Asn Lys Thr Ile Asn Ser Glu Asn Leu
    210                 215                 220

His Ile Ala Leu Tyr Leu Tyr Thr Thr
225                 230

<210> SEQ ID NO 4
<211> LENGTH: 233
<212> TYPE: PRT
<213> ORGANISM: Staphylococcus sp.

<400> SEQUENCE: 4

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Leu
        35                  40                  45

Gln His Thr Ile Leu Phe Lys Gly Phe Phe Thr Asp His Ser Trp Tyr
    50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Leu Asp Gly Lys Gln Asn Thr Val Pro Leu Glu Thr Val Lys
    130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
            180                 185                 190

Ser Val Asn Tyr Asp Leu Phe Gly Ala Gln Gly Gln Tyr Ser Asn Thr
        195                 200                 205

Leu Leu Arg Ile Tyr Arg Asp Asn Lys Thr Ile Asn Ser Glu Asn Met
    210                 215                 220
```

```
His Ile Asp Ile Tyr Leu Tyr Thr Ser
225             230
```

<210> SEQ ID NO 5
<211> LENGTH: 203
<212> TYPE: PRT
<213> ORGANISM: Staphylococcus sp.

<400> SEQUENCE: 5

```
Ala Leu His Lys Lys Ser Glu Leu Ser Thr Ala Leu Asn Asn Met
1               5                   10                  15

Lys His Ser Tyr Ala Asp Ala Asn Pro Ile Ile Gly Ala Asn Lys Ser
                20                  25                  30

Thr Gly Asp Gln Phe Leu Glu Asn Thr Leu Leu Tyr Lys Ala Phe Phe
        35                  40                  45

Leu Leu Ile Asn Phe Asn Ser Ala Glu Met Ala Gln His Phe Lys Ser
50                  55                  60

Lys Asn Val Asp Val Tyr Ala Ile Arg Tyr Ala Ala Cys Arg Thr
65              70                  75                  80

Ala Cys Thr Tyr Gly Gly Val Thr Pro His Ala Gly Asn Ala Leu Lys
                85                  90                  95

Ala Arg Lys Lys Ile Pro Ile Asn Leu Trp Ile Ile Gly Val Gln Lys
            100                 105                 110

Glu Val Ser Leu Asp Lys Val Gln Thr Asp Lys Lys Asn Val Thr Val
        115                 120                 125

Gln Glu Leu Asp Ala Gln Ala Arg Arg Tyr Leu Gln Lys Asp Leu Lys
130                 135                 140

Leu Tyr Asn Ala Ile Gln Arg Gly Lys Leu Glu Phe Asp Ser Ala Ala
145                 150                 155                 160

Ala Ser Lys Val Ser Tyr Asp Leu Phe Asp Val Ala Gly Asp Phe Pro
                165                 170                 175

Glu Lys Gln Leu Arg Ile Tyr Ser Asp Asn Lys Thr Leu Ser Thr Glu
            180                 185                 190

His Leu His Ile Asp Ile Tyr Leu Tyr Glu Ala
        195                 200
```

<210> SEQ ID NO 6
<211> LENGTH: 217
<212> TYPE: PRT
<213> ORGANISM: Staphylococcus sp.

<400> SEQUENCE: 6

```
Glu Asp Leu His Asp Lys Ser Glu Leu Thr Asp Leu Ala Leu Ala Asn
1               5                   10                  15

Ala Tyr Gly Gln Tyr Asn His Pro Phe Ile Lys Glu Asn Ile Lys Ser
                20                  25                  30

Asp Glu Ile Ser Gly Glu Lys Asp Leu Ile Phe Arg Asn Gln Gly Asp
            35                  40                  45

Ser Gly Asn Asp Leu Arg Val Lys Phe Ala Thr Ala Asp Leu Ala Gln
50                  55                  60

Lys Phe Lys Asn Lys Asn Val Asp Ile Tyr Gly Ala Ser Phe Tyr Tyr
65              70                  75                  80

Lys Cys Glu Lys Ile Ser Glu Asn Ile Ser Glu Cys Leu Tyr Gly Gly
                85                  90                  95

Thr Thr Leu Asn Ser Glu Lys Leu Ala Gln Glu Arg Val Ile Gly Ala
            100                 105                 110
```

-continued

```
Asn Val Trp Val Asp Gly Ile Gln Lys Glu Thr Glu Leu Ile Arg Thr
        115                 120                 125
Asn Lys Lys Asn Val Thr Leu Gln Glu Leu Asp Ile Lys Ile Arg Lys
    130                 135                 140
Ile Leu Ser Asp Lys Tyr Lys Ile Tyr Tyr Lys Asp Ser Glu Ile Ser
145                 150                 155                 160
Lys Gly Leu Ile Glu Phe Asp Met Lys Thr Pro Arg Asp Tyr Ser Phe
                165                 170                 175
Asp Ile Tyr Asp Leu Lys Gly Glu Asn Asp Tyr Glu Ile Asp Lys Ile
            180                 185                 190
Tyr Glu Asp Asn Lys Thr Leu Lys Ser Asp Asp Ile Ser His Ile Asp
        195                 200                 205
Val Asn Leu Tyr Thr Lys Lys Lys Val
    210                 215

<210> SEQ ID NO 7
<211> LENGTH: 233
<212> TYPE: PRT
<213> ORGANISM: Staphylococcus sp.

<400> SEQUENCE: 7

Ser Glu Lys Ser Glu Glu Ile Asn Glu Lys Asp Leu Arg Lys Lys Ser
1               5                   10                  15
Glu Leu Gln Arg Asn Ala Leu Ser Asn Leu Arg Gln Ile Tyr Tyr Tyr
            20                  25                  30
Asn Glu Lys Ala Ile Thr Glu Asn Lys Glu Ser Asp Asp Gln Phe Leu
        35                  40                  45
Glu Asn Thr Leu Leu Phe Lys Gly Phe Phe Thr Gly His Pro Trp Tyr
    50                  55                  60
Asn Asp Leu Leu Val Asp Leu Gly Ser Lys Asp Ala Thr Asn Lys Tyr
65                  70                  75                  80
Lys Gly Lys Lys Val Asp Leu Tyr Gly Ala Tyr Tyr Gly Tyr Gln Cys
                85                  90                  95
Ala Gly Gly Thr Pro Asn Lys Thr Ala Cys Met Tyr Gly Gly Val Thr
            100                 105                 110
Leu His Asp Asn Asn Arg Leu Thr Glu Glu Lys Lys Val Pro Ile Asn
        115                 120                 125
Leu Trp Ile Asp Gly Lys Gln Thr Thr Val Pro Ile Asp Lys Val Lys
    130                 135                 140
Thr Ser Lys Lys Glu Val Thr Val Gln Glu Leu Asp Leu Gln Ala Arg
145                 150                 155                 160
His Tyr Leu His Gly Lys Phe Gly Leu Tyr Asn Ser Asp Ser Phe Gly
                165                 170                 175
Gly Lys Val Gln Arg Gly Leu Ile Val Phe His Ser Ser Glu Gly Ser
            180                 185                 190
Thr Val Ser Tyr Asp Leu Phe Asp Ala Gln Gly Gln Tyr Pro Asp Thr
        195                 200                 205
Leu Leu Arg Ile Tyr Arg Asp Asn Lys Thr Ile Asn Ser Glu Asn Leu
    210                 215                 220
His Ile Asp Leu Tyr Leu Tyr Thr Thr
225                 230
```